(12) United States Patent
Neel et al.

(10) Patent No.: US 8,388,906 B2
(45) Date of Patent: Mar. 5, 2013

(54) APPARATUS FOR DISPENSING TEST STRIPS

(75) Inventors: Gary T. Neel, Weston, FL (US); Brent E. Modzelewski, Boca Raton, FL (US); George R. Rounds, Coconut Creek, FL (US); Carlos Oti, Plantation, FL (US); Allan Javier Caban, Lake Worth, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 104 days.

(21) Appl. No.: 11/930,862

(22) Filed: Oct. 31, 2007

(65) Prior Publication Data

US 2008/0118400 A1 May 22, 2008

Related U.S. Application Data

(63) Continuation-in-part of application No. 11/373,284, filed on Mar. 13, 2006.

(51) Int. Cl.
*G01N 33/52* (2006.01)

(52) U.S. Cl. ............... 422/401; 422/82.01; 422/104; 422/102; 422/55; 422/58; 600/583; 600/584; 204/403.01

(58) Field of Classification Search .............. 600/583; 422/50, 61, 67, 68.1, 99, 102, 104
See application file for complete search history.

(56) References Cited

U.S. PATENT DOCUMENTS

| | | | |
|---|---|---|---|
| 3,582,335 A | 6/1971 | Erlichman | |
| 3,918,910 A | 11/1975 | Soya et al. | |
| 4,100,559 A | 7/1978 | Wareham et al. | |
| 4,142,863 A | 3/1979 | Covington et al. | |
| 4,279,861 A | 7/1981 | Jessop | |
| 4,834,234 A | 5/1989 | Sacherer et al. | |
| 4,911,344 A | 3/1990 | Kahler | |
| 5,102,624 A | 4/1992 | Muraishi | |
| 5,154,889 A | 10/1992 | Muraishi | |
| 5,244,116 A * | 9/1993 | Leo ............................ | 221/232 |
| 5,281,395 A | 1/1994 | Markart et al. | |
| 5,298,425 A | 3/1994 | Kuhn et al. | |
| 5,489,414 A | 2/1996 | Schreiber et al. | |
| 5,505,308 A | 4/1996 | Eikmeier et al. | |
| 5,510,266 A | 4/1996 | Bonner et al. | |

(Continued)

FOREIGN PATENT DOCUMENTS

DE 10 2004 062 255 B3 2/2006
EP 0 059 350 A1 9/1982

(Continued)

OTHER PUBLICATIONS

International Search Report and Written Opinion, PCT/US2007/005079, dated Sep. 3, 2007.

(Continued)

*Primary Examiner* — Sally Merkling
(74) *Attorney, Agent, or Firm* — Finnegan, Henderson, Farabow, Garrett & Dunner LLP

(57) ABSTRACT

A container for a diagnostic testing system consists essentially of a media dispenser embedded in the container and configured to house a plurality of test media; a first positioning device arranged on or near a first surface of the media dispenser and configured to push the plurality of test media toward a second surface of the media dispenser; and a meter for performing a diagnostic test on a sample applied to one of the plurality of test media, the meter including a closure portion configured to close the container.

20 Claims, 30 Drawing Sheets

U.S. PATENT DOCUMENTS

| | | | |
|---|---|---|---|
| 5,575,403 | A | 11/1996 | Charlton et al. |
| 5,609,823 | A | 3/1997 | Harttig et al. |
| 5,630,986 | A | 5/1997 | Charlton et al. |
| 5,660,791 | A | 8/1997 | Brenneman et al. |
| 5,679,311 | A | 10/1997 | Harttig et al. |
| 5,714,123 | A | 2/1998 | Sohrab |
| 5,720,924 | A | 2/1998 | Eikmeier et al. |
| 5,797,693 | A | 8/1998 | Jaeger |
| 5,810,199 | A | 9/1998 | Charlton et al. |
| 5,854,074 | A | 12/1998 | Charlton et al. |
| 5,856,195 | A | 1/1999 | Charlton et al. |
| 5,863,800 | A | 1/1999 | Eikmeier et al. |
| 5,872,713 | A | 2/1999 | Douglas et al. |
| 5,989,197 | A | 11/1999 | Avaltroni |
| 5,989,917 | A | 11/1999 | McAleer et al. |
| 6,106,780 | A | 8/2000 | Douglas et al. |
| 6,168,957 | B1 | 1/2001 | Matzinger et al. |
| 6,176,119 | B1 | 1/2001 | Kintzig |
| 6,283,982 | B1 | 9/2001 | Levaughn et al. |
| 6,377,894 | B1 | 4/2002 | Deweese et al. |
| 6,398,067 | B1 | 6/2002 | Belfance et al. |
| 6,428,664 | B1 | 8/2002 | Bhullar et al. |
| 6,472,220 | B1 | 10/2002 | Simons et al. |
| 6,488,828 | B1 | 12/2002 | Bhullar et al. |
| 6,508,380 | B1 | 1/2003 | von Schuckmann |
| 6,534,017 | B1 | 3/2003 | Bottwein et al. |
| 6,544,475 | B1 | 4/2003 | Douglas et al. |
| 6,558,528 | B1 | 5/2003 | Matzinger |
| 6,682,704 | B2 | 1/2004 | Bottwein et al. |
| 7,063,234 | B2 | 6/2006 | Giraud |
| 7,070,053 | B1 | 7/2006 | Abrams et al. |
| 7,138,089 | B2 * | 11/2006 | Aitken et al. ............ 422/82.01 |
| 7,213,720 | B2 | 5/2007 | Giraud |
| 7,276,027 | B2 | 10/2007 | Haar et al. |
| 2002/0057993 | A1 | 5/2002 | Maisey et al. |
| 2002/0076349 | A1 | 6/2002 | Aitken et al. |
| 2002/0104849 | A1 | 8/2002 | Giruad |
| 2002/0188224 | A1 | 12/2002 | Roe et al. |
| 2003/0031591 | A1 | 2/2003 | Whitson et al. |
| 2003/0031595 | A1 | 2/2003 | Kirchhevel et al. |
| 2003/0032190 | A1 | 2/2003 | Brown et al. |
| 2003/0036200 | A1 * | 2/2003 | Charlton ..................... 436/43 |
| 2003/0047451 | A1 | 3/2003 | Bhullar et al. |
| 2003/0059350 | A1 | 3/2003 | Sacherer |
| 2003/0089730 | A1 | 5/2003 | May et al. |
| 2003/0116583 | A1 | 6/2003 | Pugh |
| 2003/0129346 | A1 | 7/2003 | Pearson et al. |
| 2003/0133847 | A1 | 7/2003 | Hagen et al. |
| 2003/0175155 | A1 | 9/2003 | Charlton |
| 2003/0178437 | A1 | 9/2003 | Crawford |
| 2003/0185705 | A1 | 10/2003 | Otake |
| 2003/0185708 | A1 | 10/2003 | Otake |
| 2003/0186446 | A1 | 10/2003 | Pugh |
| 2003/0191415 | A1 | 10/2003 | Moerman et al. |
| 2003/0203498 | A1 | 10/2003 | Neel et al. |
| 2003/0211619 | A1 | 11/2003 | Olson et al. |
| 2003/0212344 | A1 | 11/2003 | Yuzhakov et al. |
| 2003/0212345 | A1 | 11/2003 | McAllister et al. |
| 2003/0219357 | A1 | 11/2003 | Douglas et al. |
| 2003/0223906 | A1 | 12/2003 | McAllister et al. |
| 2004/0007585 | A1 | 1/2004 | Griffith et al. |
| 2004/0038411 | A1 | 2/2004 | Hayter et al. |
| 2004/0048394 | A1 | 3/2004 | Kirchhevel |
| 2004/0057878 | A1 | 3/2004 | House et al. |
| 2004/0178216 | A1 | 9/2004 | Brickwood et al. |
| 2005/0019953 | A1 | 1/2005 | Groll |
| 2005/0023137 | A1 | 2/2005 | Bhullar et al. |
| 2005/0143675 | A1 | 6/2005 | Neel et al. |
| 2006/0189895 | A1 | 8/2006 | Neel et al. |
| 2007/0212258 | A1 | 9/2007 | Neel et al. |
| 2008/0134810 | A1 | 6/2008 | Neel et al. |

FOREIGN PATENT DOCUMENTS

| | | |
|---|---|---|
| EP | 0 064 691 A1 | 11/1982 |
| EP | 0 064 691 B1 | 3/1986 |
| EP | 0 255 675 B1 | 5/1992 |
| EP | 0 732 590 A2 | 9/1996 |
| EP | 0 732 590 A3 | 5/1997 |
| EP | 779 226 A1 | 6/1997 |
| EP | 0 622 119 B1 | 11/1999 |
| EP | 1 022 565 A2 | 7/2000 |
| EP | 1 225 448 A2 | 7/2002 |
| EP | 1 285 695 A2 | 2/2003 |
| EP | 1 286 162 A2 | 2/2003 |
| EP | 1 329 395 A1 | 7/2003 |
| EP | 1 362 801 A2 | 11/2003 |
| EP | 1 369 083 A1 | 12/2003 |
| EP | 1 806 588 A1 | 7/2007 |
| WO | WO 94/10558 | 5/1994 |
| WO | WO 94/29703 A1 | 12/1994 |
| WO | WO 97/29847 A1 | 8/1997 |
| WO | WO 01/23885 A1 | 4/2001 |
| WO | WO 02/08753 A2 | 1/2002 |
| WO | WO 02/055008 A2 | 7/2002 |
| WO | WO 02/078533 A2 | 10/2002 |
| WO | WO 03/042691 A1 | 5/2003 |
| WO | WO 03/082091 A2 | 10/2003 |
| WO | WO 03/082092 A1 | 10/2003 |
| WO | WO 03/083469 A2 | 10/2003 |
| WO | WO 2004/011068 A1 | 2/2004 |
| WO | WO 2004/041082 A1 | 5/2004 |
| WO | WO 2004/041672 A2 | 5/2004 |
| WO | WO 2004/044142 A2 | 5/2004 |
| WO | WO 2005/040793 A1 | 5/2005 |
| WO | WO 2006/076721 A2 | 7/2006 |
| WO | WO 2007/050396 A1 | 5/2007 |
| WO | WO 2007/085438 A2 | 8/2007 |
| WO | WO 2007/090662 A1 | 8/2007 |
| WO | WO 2007/108900 A1 | 9/2007 |
| WO | WO 2008/063405 A1 | 5/2008 |

OTHER PUBLICATIONS

XP-002397571, "ACCU-CHEK® Compact Plus User's Manual," Roche Diagnostics GmbH, Jan. 2005.

International Search Report and Written Opinion for PCT/US2008/081691, mailed Jan. 29, 2009.

Office Action dated Jun. 9, 2009, filed in U.S. Appl. No. 11/373,284, filed Mar. 13, 2006.

International Search Report mailed Oct. 8, 2009 from the European Patent Office in corresponding Application No. PCT/US2008/081432.

Office Action mailed Jul. 20, 2010, in co-pending U.S. Appl. No. 11/373,284, filed Mar. 13, 2006.

Office Action mailed Feb. 12, 2010, in co-pending U.S. Appl. No. 11/373,284, filed Mar. 13, 2006.

* cited by examiner

APPARATUS FOR DISPENSING TEST STRIPS

CROSS-REFERENCE TO RELATED APPLICATIONS

This application is a continuation-in-part of and claims priority to U.S. patent application Ser. No. 11/373,284, filed on Mar. 13, 2006, the entire content of which is incorporated herein by reference.

BACKGROUND OF THE INVENTION

1. Technical Field

The present invention relates to the field of diagnostic testing and, more particularly, to diagnostic testing systems using electronic meters.

2. Background

Diagnostic testing systems are commonly used to perform various types of diagnostic tests on various types of samples. The diagnostic test may be a qualitative or quantitative test to determine the presence, concentration or amount of one or more analytes in a sample. The analyte may be a medically significant analyte—e.g., glucose, ketones, cholesterol, triglycerides, human choriogonadotropin (HCG), hemoglobin A1C, fructosamine, carbohydrates, tumor markers, lead, anti-epilepsy drugs, bilirubin, liver function markers, toxins or their metabolites, controlled substances, blood coagulation factors (PT, ATPP), etc.—contained in a biological sample—e.g., blood, urine, tissue, saliva, etc. However the diagnostic test is not limited to the medical field. In addition, diagnostic test meters can be used to monitor analytes or chemical parameters in non-medical samples such as water, soil, sewage, sand, air, or any other suitable sample.

Such diagnostic testing systems may include a test media (e.g., a test strip, tab, disc, etc.) configured to react to the presence of the analyte in a sample, and a separate electronic meter configured to interface with the test media in order to conduct the diagnostic test and indicate the results of the diagnostic test to the user.

In order to conduct the diagnostic test, a user must first obtain a sample test media, e.g., a test strip, from a container, then obtain a sample using a sampling device (e.g., by drawing blood using a lancet), and then apply the sample to the test media (either before or after inserting the test media into the meter interface). The meter then performs the diagnostic test on the sample and indicates the result to the user, e.g., using a numerical display.

Prior art diagnostic meters are sometimes bulky because the housings contain the display, electronics, and test media. In addition, the user of a blood testing diagnostic system must manage and carry not only the meter, but also a test media container and a sampling device. These three components must be manipulated in a certain order, and require a substantial amount of attention and manipulation to conduct a successful test. Not only are the steps cumbersome to some users, there exists the possibility that the test media container, sampling device and meter could be separated from each other, so that the user may find themselves without one or more of the components necessary to conduct the diagnostic test.

As is known in the art, test media from different manufacturers or media from different manufacturing lots may respond differently to the presence or concentration of analyte in the sample. In order to obtain more accurate results, the electronic meter may be calibrated with respect to a given test strip from a brand or lot of test strips by providing it with one or more brand- or lot-specific calibration parameters that correlate the signal response from a particular brand or lot of test media to a standardized reference. By such calibration, the results reported by the meter more accurately represent the amount of analyte in a sample.

Before running a diagnostic test, the meter needs to be properly calibrated. The user may be required to provide the meter with the appropriate calibration parameters in a separate "coding" step. For example, the test media container may bear a code number which is entered into the meter, and from which the meter can access the appropriate calibration information stored in the meter's memory. The code number can be entered manually (e.g., using buttons or other user input devices on the meter) so as to provide the calibration data to the meter. Alternatively, the calibration data may be downloaded, e.g., from a manufacturer's website. In another approach, the test media container may be provided with an associated code chip, e.g. a ROM, in which the calibration data is stored electronically. The user may provide the calibration data to the meter by inserting the code chip into a corresponding port on the meter.

These prior art coding methods can be inconvenient or difficult for the user. For example, elderly or infirm users may have difficulty downloading calibration data or inserting code chips, which must be physically aligned properly in order to achieve a data connection with the meter. Code chips can be misplaced or lost, leading to the inability to use corresponding test media, or using the test media with an unmatched coding device. Further, users may forget to calibrate the meter for use with a new brand or lot of test media. Consequently, the user may enter incorrect calibration parameters or codes, or the user may use test media from one brand or lot with a meter calibrated for use with test media from a different brand or lot. Once a meter is calibrated for a given lot of test media, the use of that meter with test media from another lot may lead to erroneous results that could have serious consequences for the user. For instance, where the test is a self-test of blood glucose level, an erroneous result could lead the user to act, or fail to act, in a manner detrimental to his or her health.

A possible solution to the above-mentioned coding problems is to insure that all marketed media behave the same. This approach is referred to as "universal coding." Universal coding schemes use strip lots that are controlled and sorted to a narrow acceptance criteria, i.e. all strips are conformed to a single set of calibration parameters, thus eliminating the needs for multiple sets of parameters to be stored in the meter 130. Universal coding saves the cost of replacing the meter 130 by allowing it to be used with many different test strip containers 110. From a manufacturing perspective, universally coded media 120 needs to be tightly controlled such that manufactured strip lots have the same behavior, and hence code, in order to fit the meter's fixed calibration data. This method is not technique dependent and helps prevent errors due to mixed strip lots. Furthermore, universal coding always has the correct code such that there is no miss-match between the meter 130 and the strip lot code. However, the narrow limits imposed by this method do not conform well to large-scale manufacturing processes, which include inherent variances. It is nearly impossible using high-throughput, batch-oriented manufacturing techniques to ensure that test media will exhibit perfectly consistent behavior, thus the universal coding scheme invariably results in non-conforming lots of media. This media will be unusable, adding to cost and undesirable waste.

Accordingly, there is a need for diagnostic testing systems that are convenient to carry and that minimize the chance that a user will use a diagnostic meter with test media from a brand or lot for which the meter has not been calibrated.

SUMMARY OF THE INVENTION

The illustrative embodiments described herein meet these and other needs by providing a container for a diagnostic testing system, consisting essentially of the combination of the following three basic and novel features (1) a media dispenser embedded in the container and configured to house a plurality of test media; (2) a first positioning device arranged on or near a first surface of the media dispenser and configured to push the plurality of test media toward a second surface of the media dispenser; and (3) a meter for performing a diagnostic test on a sample applied to one of the plurality of test media, the meter including a closure portion configured to close the container.

The illustrative embodiments described herein also meet these and other needs by providing a container for a diagnostic testing system, consisting essentially of the combination of the following four basic and novel features (1) a container for a diagnostic testing system consists essentially of a media dispenser removably arranged in the container and configured to house a plurality of test media; (2) a first positioning device arranged on or near a first surface of the media dispenser and configured to push the plurality of test media toward a second surface of the media dispenser; (3) a second positioning device arranged between a bottom exterior surface of the media dispenser and a bottom interior surface of the container; and (4) a meter for performing a diagnostic test on a sample applied to one of the plurality of test media, the meter including a closure portion configured to close the container.

The illustrative embodiments further provide a meter housing with a receptacle that can receive a test strip container. Additionally, the meter housing may also receive devices such as media players, terrestrial or satellite radios, travel alarm clocks, test alarms, memo voice recorders, PDAs, cell phones, or other add-on functionality, such that a code, similar to one placed on the test strip container, can be read in order for the device to be used in conjunction with the meter.

Illustrative embodiments of the present invention can also provide a refillable test strip container with an integrated meter. A separate foil pouch of test strips, and optionally desiccant, can be placed into the container as a refill. This integrated system is advantageous in that both the meter and the container can always be reused, allowing for more efficient marketing and packaging, and also more variety in container shapes and designs.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

1. The Integrated System

Figure 1:
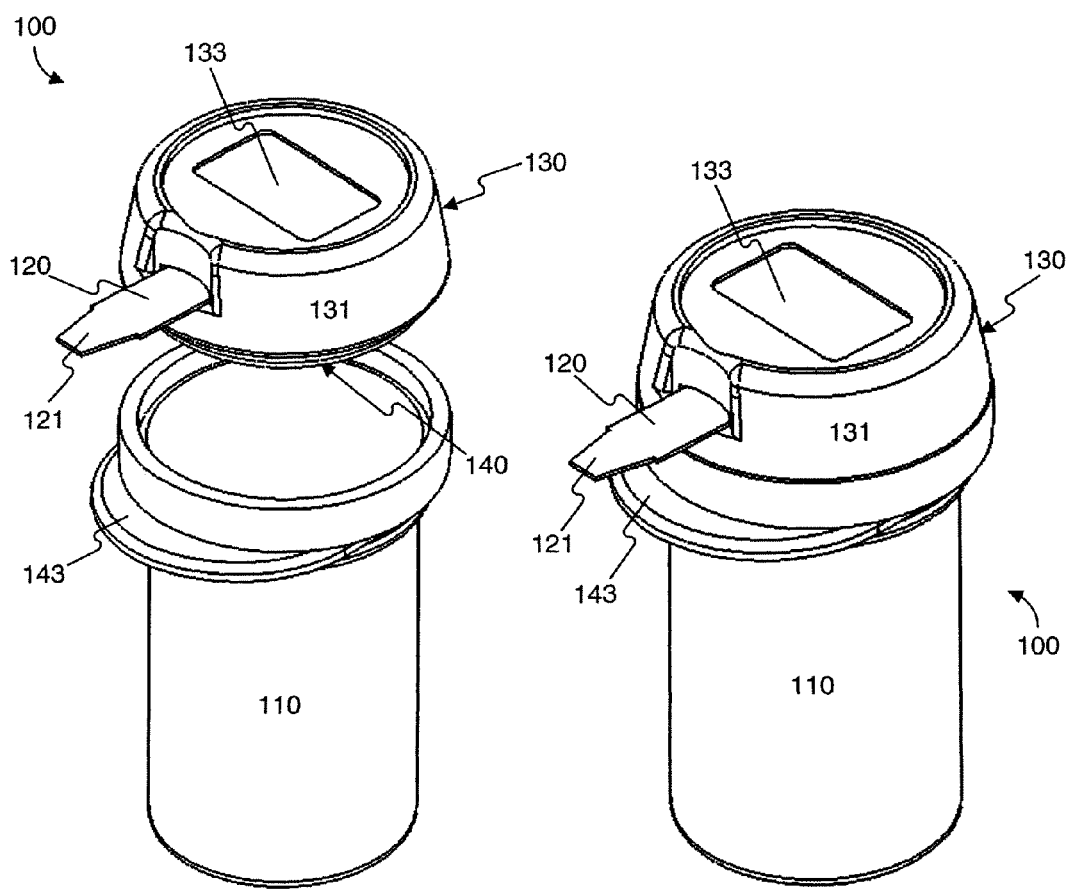
FIG. 1 is a perspective view of a first embodiment of an integrated system consistent with the present invention.

FIG. 1 is an integrated system 100 for conducting a diagnostic test in accordance with an exemplary embodiment of the present invention. Exemplary integrated system 100 includes a container 110 for containing test media, such as test strips 120, and a meter 130 for performing a diagnostic test using the test strips 120 contained in container 110.

Figure 3:
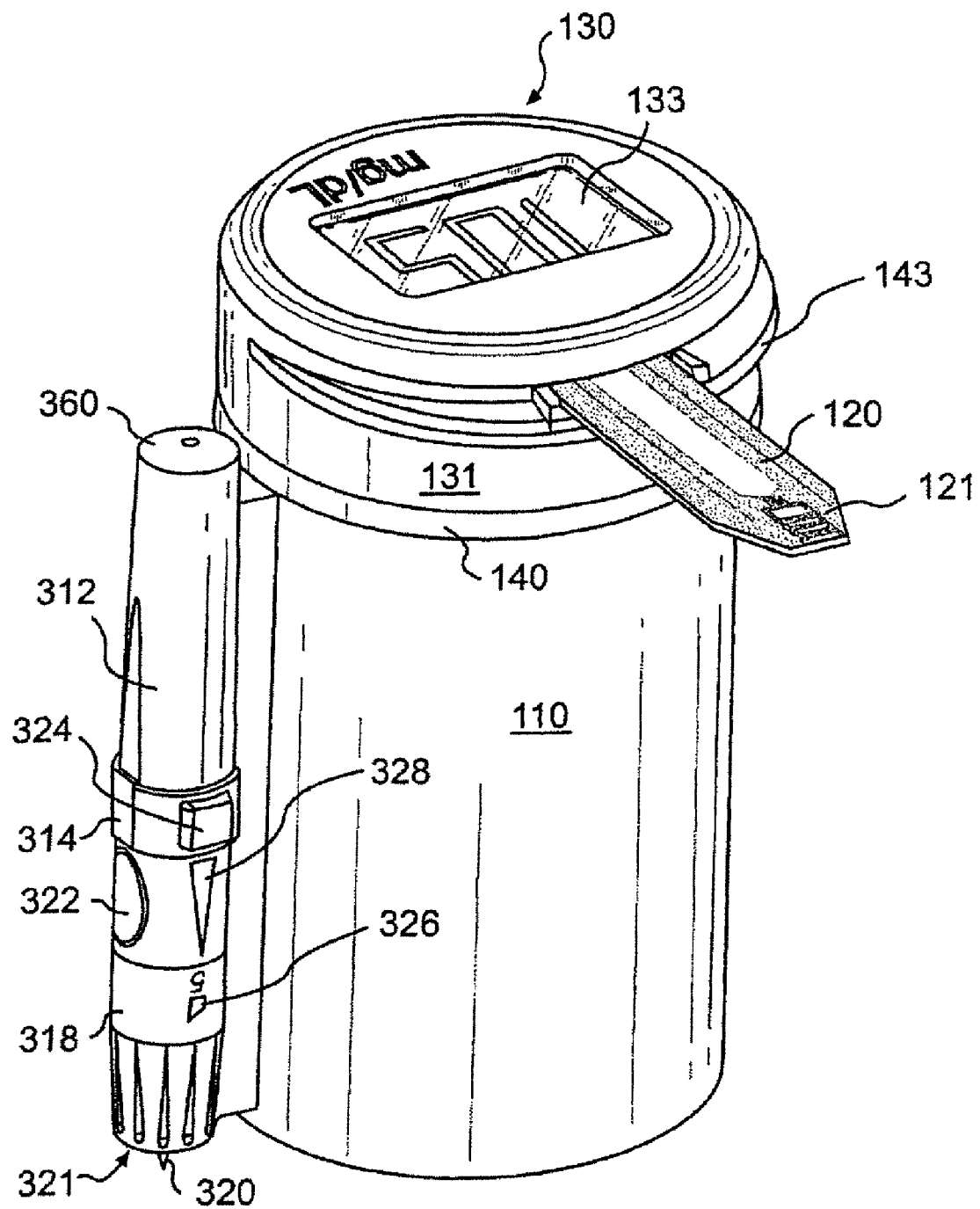
FIG. 3 is a perspective view of a third embodiment of an integrated system consistent with the present invention.

In one illustrative embodiment, the diagnostic test is the determination of the amount of glucose in a sample of whole blood applied to a sample chamber 121 of test strip 120, as depicted in FIG. 3. For blood glucose testing, meter 130 may employ any of a variety of techniques. Illustratively, the diagnostic test employs an electrochemical technique (e.g., coulometry, amperometry, potentiometry, etc.). Exemplary electrochemical systems are described in prior U.S. Pat. No. 6,743,635, issued Jun. 1, 2004, and U.S. Pat. No. 6,946,299, issued Sep. 20, 2005, both entitled "SYSTEM AND METHOD FOR BLOOD GLUCOSE TESTING" and both having an assignee in common with the instant application, which are incorporated by reference herein in their entirety. Alternatively, meter 130 may employ a photometric technique (e.g., reflection, transmission, scattering, absorption, fluorescence, electro-chemiluminescence, etc.) to determine the amount of glucose in the sample. Exemplary photometric systems are described in U.S. Pat. Nos. 6,201,607, 6,284,550 and 6,541,266, each commonly-assigned with the instant application, which are incorporated by reference herein in their entirety. However, electrochemical techniques are currently preferred because, among other reasons, they require a smaller blood sample (on the order of 1 μL or less) than the photometric techniques (on the order of 1 μL or greater). Further, the instrumentation for the electrochemical techniques typically requires less power and can typically be made more compactly than the instrumentation for the photometric techniques.

Integrated system 100 will be illustrated with reference to a diagnostic test to determine the concentration of blood glucose using an electrochemical technique, with the understanding that the principles of the present invention are equally above. Further, although the present invention has been illustrated as utilizing test media in the form of test strips 120, exemplary embodiments of the present invention are not limited to a particular type of media and those of skill in the art will recognize that the principles of the present invention are equally applicable to diagnostic testing systems which employ test media in other forms, e.g., tabs, discs, etc.

Figure 4:
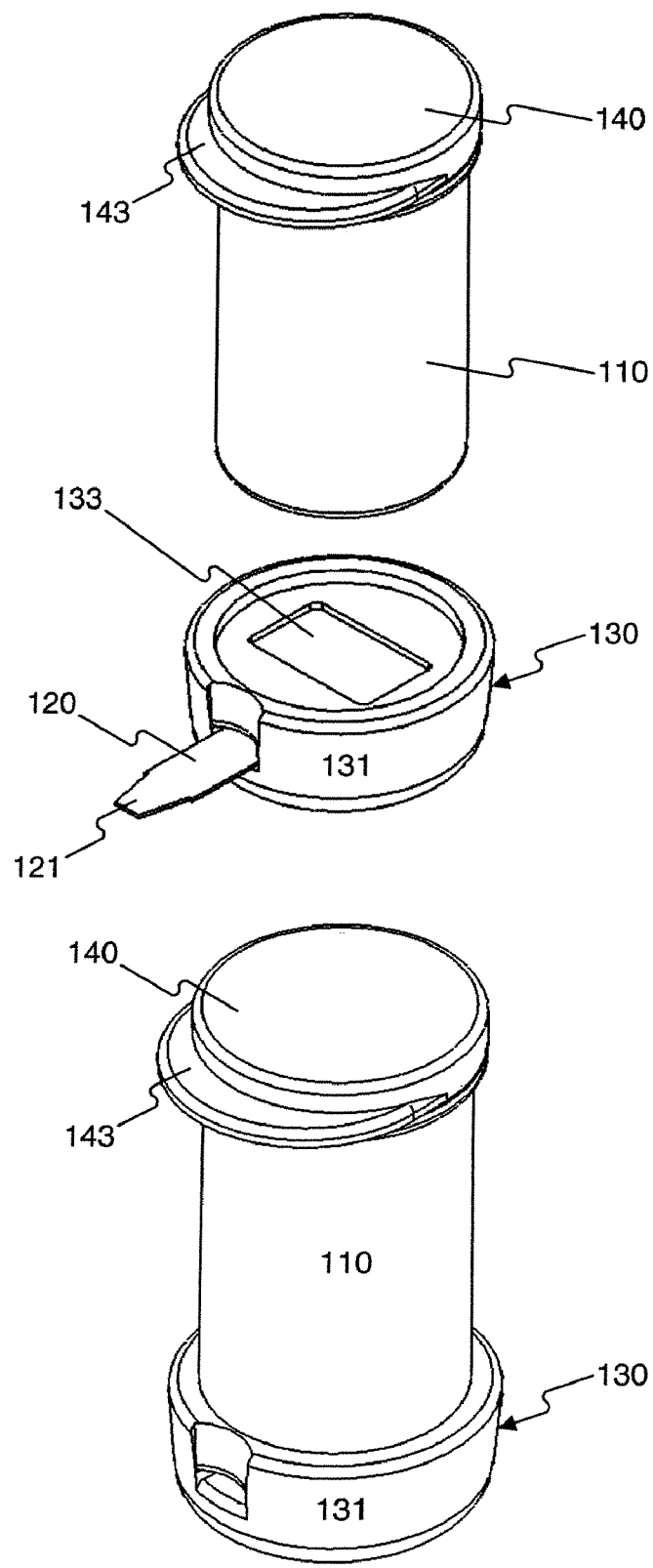
FIG. 4 is a cross-sectional view of a fourth embodiment of an integrated system consistent with the present invention.
Figure 5:
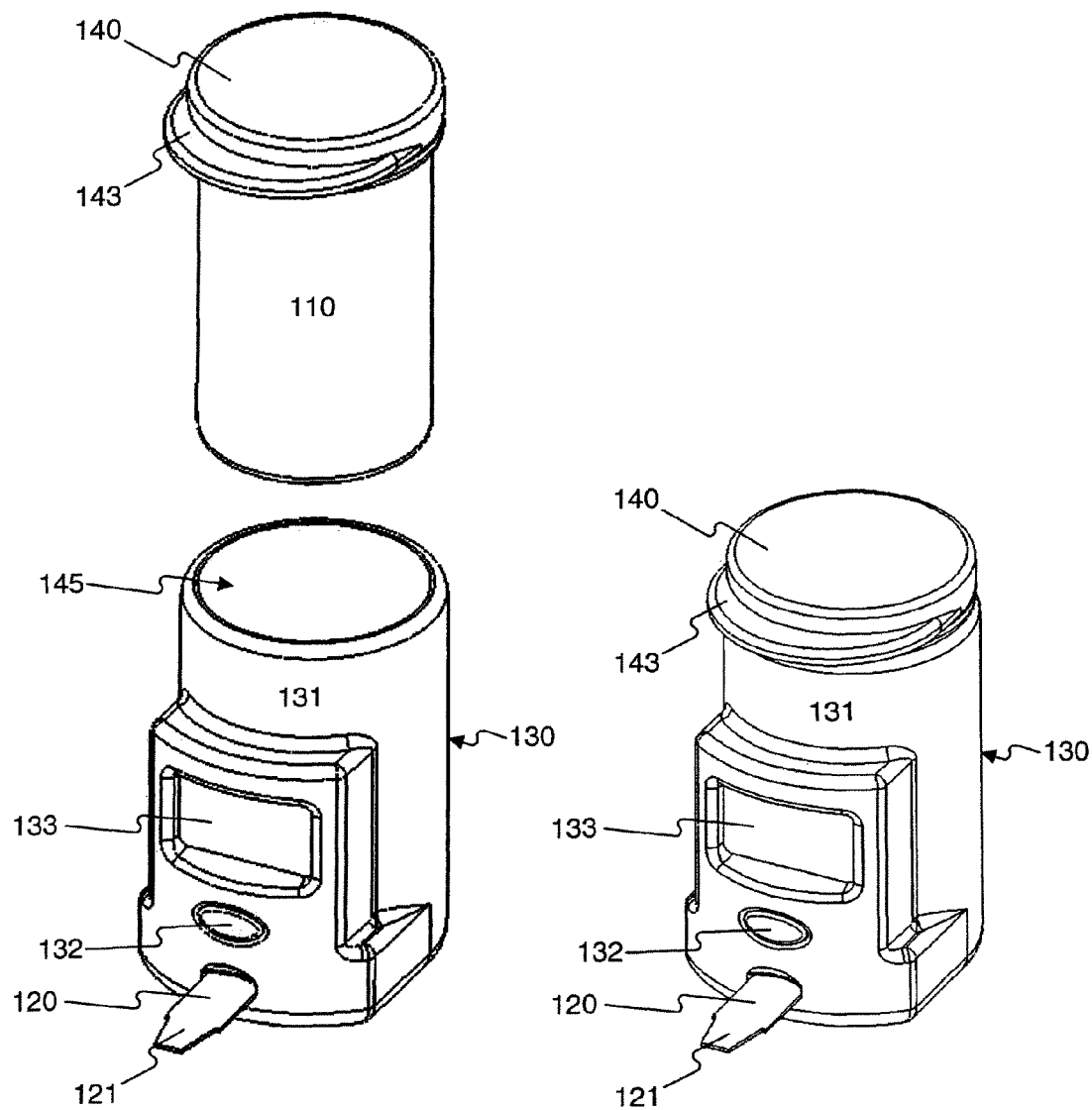
FIG. 5 is a perspective view of a fifth embodiment of an integrated system consistent with the present invention.
Figure 6:
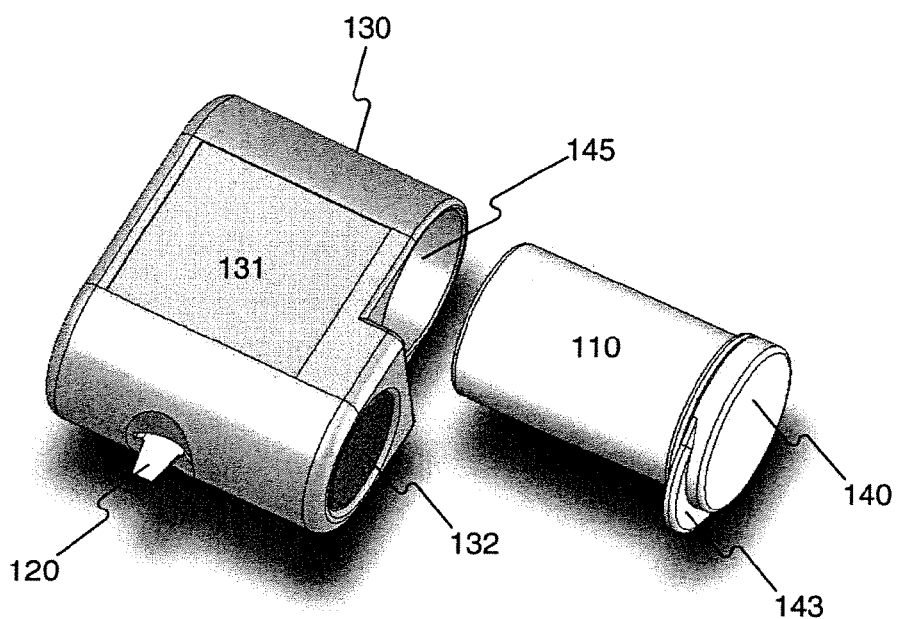
FIG. 6 is a perspective view of a sixth embodiment of an integrated system consistent with the present invention.
Figure 6:
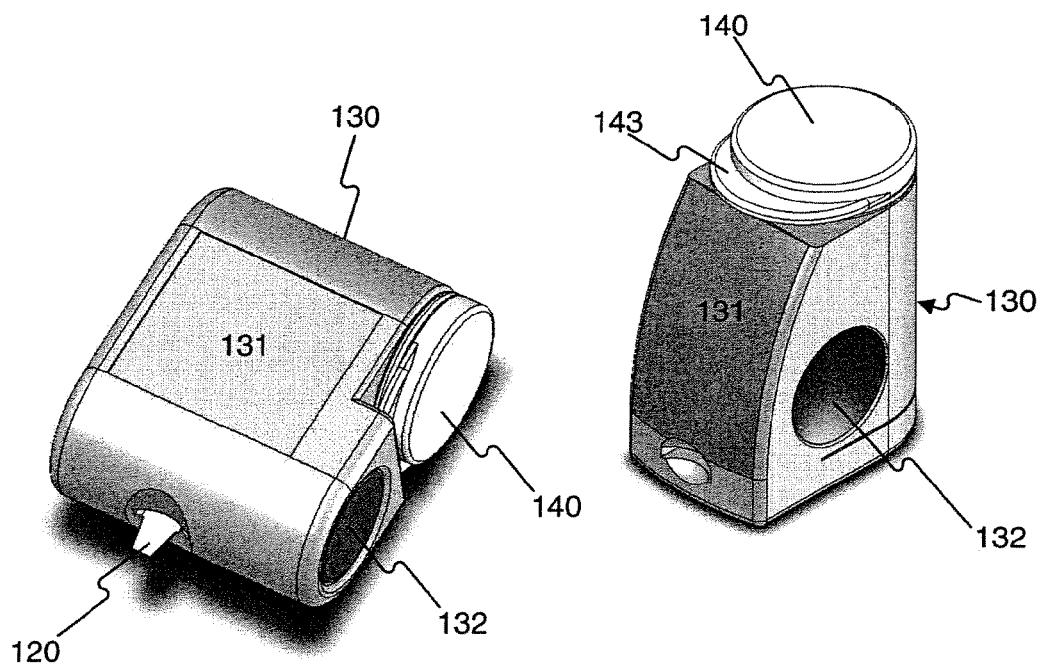

Meter 130 may be contained within a housing 131. The meter housing 131 is attached to or otherwise includes a closure portion 140 (bottom of meter 130 in FIG. 1) which engages container 110 in order to selectively close an opening 111 of the container. As would be apparent to one of ordinary skill in the art, and as discussed herein, attached may be used to signify affiliated with, associated with, affixed with/to, connected with/to, coupled with/to, fastened with/to, fixed with/to, secured with/to, etc. Alternatively, as illustrated in FIG. 4, a bottom portion of container 110 may be attached to meter housing 131 by means of a retainer clip, screw thread, snap, or other retaining methods (not shown) or may be inserted into receptacle 145 of meter housing 131 in a keyed locating position, wherein the meter 130 is keyed to align with the container 110 such that it lines up with the code placement in order for the container to be read accurately (FIGS. 5 and 6). One having ordinary skill in the art will understand that meter housing 131 with receptacle 145 can additionally receive coded devices such as media players, terrestrial or satellite radios, travel alarm clocks, test alarms, PDAs, cell phones, memo voice recorders or other add-on functionality, such that a code, similar to the one placed on container 110, can be read in order for the device to be used in conjunction with meter 130.

In an illustrative embodiment, meter housing 131 may include one or more buttons 132 implemented by a user control function to turn on meter 130 or eject container 110 after use. As illustrated in FIG. 5, button 132 may be comfortably pressed with the right thumb or index finger while the integrated system 100 is held in the right hand, with display 133 in an upright position. However, button 132 may be positioned elsewhere on meter 130. For example, button 132 may be placed on a right hand side of the meter housing 131 in order to be more convenient for left handed users (FIG. 27) or on a top portion of the meter 130.

Figure 7:
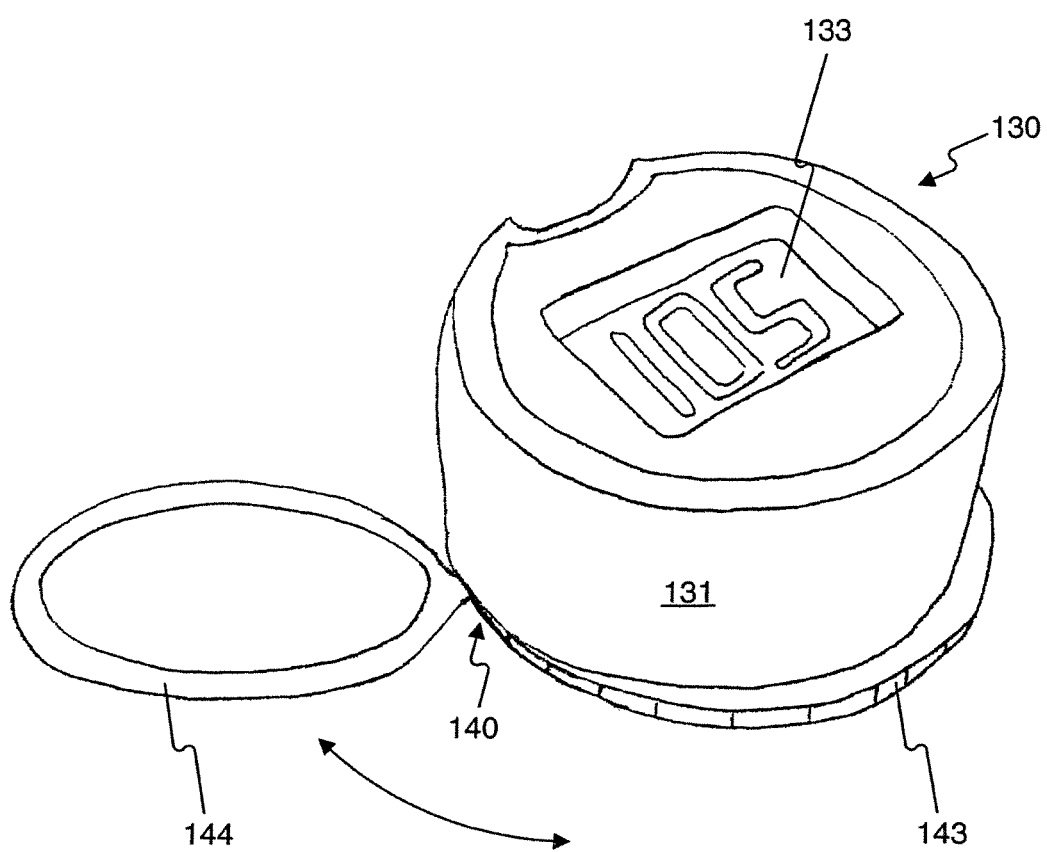
FIG. 7 is a perspective view of a meter housing comprising a holder configured to receive one or more devices used for diagnostic testing.

Meter housing 131 may additionally include a holder 144 that is configured to receive one or more containers 110, as illustrated in FIG. 7. Holder 144 is configured to be stored underneath closure 140 when not in use and is slidably movable (as illustrated by the position arrow) to a side position of the container 110 in order to receive and hold additional containers 110. In an illustrative embodiment, meter housing 131 has one side (e.g., the bottom of meter housing 131 in FIG. 1) which is shaped to conform to the closure 140 and is affixed to the closure 140, e.g., by a mechanical attachment (clips, etc.), bonding, gluing, welding, etc. Alternatively, closure portion 140 may be formed integrally with the meter housing 131. The meter 130 and closure 140 together thus form a cap or lid for the container 110.

The closure 140 may be configured to engage the container in a number of ways. In the closed position (see FIGS. 3 and 4), closure 140 closes opening 111 sufficiently to prevent loss or removal of the test media from container 110. Accordingly, closure 140 is configured to engage container 110 so as to prevent test strips 120 from passing through opening 111 when closure 140 is in the closed position. Container 110 and closure 140 may also be configured to prevent the infiltration of light, liquid, vapor, and/or air into the container 110 so as to prevent contamination or degradation of the test media. Where the test media is configured such that it is toxic or may present a choking hazard, closure 140 may optionally be configured to be child-resistant in order to prevent children from opening container 110 and accessing the test media. For example, closure 140 and container 110 may be configured in a manner similar to well known child-resistant containers for pharmaceuticals or household chemicals.

Figure 2:
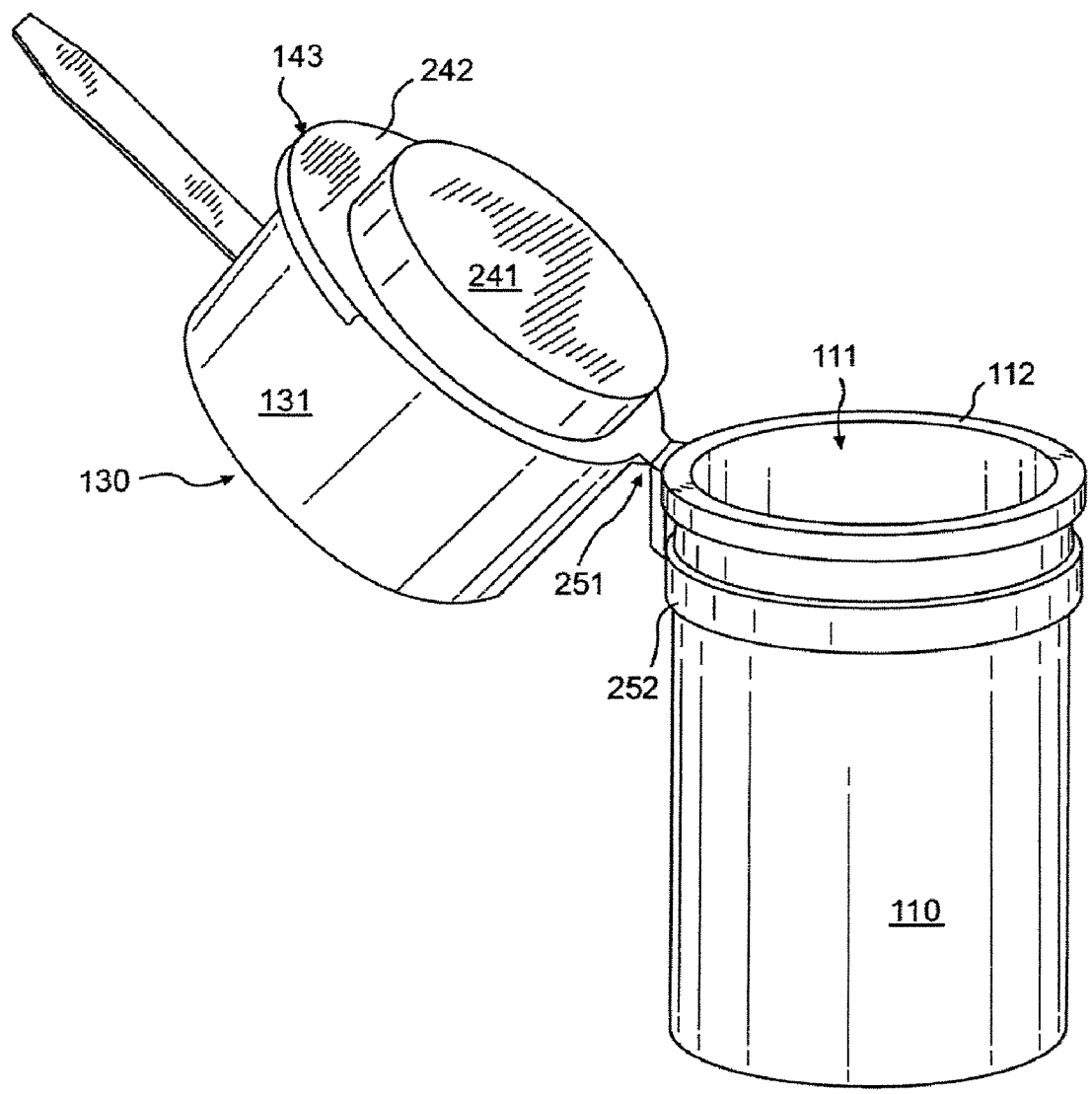
FIG. 2 is a perspective view of a second embodiment of an integrated system consistent with the present invention.

Closure 140 may be configured as a twist-off cap, e.g., by providing inter-engaging threads (not shown) on the closure 140 and the container 110. Alternatively, closure 140 may be configured to slide over the opening, e.g., within grooves (not shown) beside the opening. As a further alternative, closure 140 may be provided with a catch (not shown), such as a detent, that engages container 110 (or vice versa). The catch may be released by a button. However, in an illustrative embodiment, the closure 140 is configured to form a press-fit seal with the container so as to seal the opening against the infiltration of light, liquid and vapor. For example, in FIG. 1, closure 140 is configured with a recess (not shown) to press-fit to the outside of the opening 111, so that the rim of the opening 111 fits within the closure portion 140. Alternatively, closure 140 may be configured with a projection 241 shaped to engage the inside of the opening 111, as shown in FIG. 2. However, it will be understood that the present invention is not limited to any particular configuration of the container and closure and that other configurations may be employed consistent with the principles of the present invention.

For ease of manufacture, opening 111 may be made in the same shape as the container 110. For instance, the housing 131 of meter 130 will also have an exterior shape similar to that of the container 110 so that the integrated system 100 may be more comfortably held and carried, e.g., in a user's pocket. However, it will be understood that the container 110, meter 130 and opening 111 need not be of the same exterior shape, and the container 110 and meter 130 may be configured in different shapes without departing from the scope of the present invention.

Illustratively, the container 110 is generally a right circular cylinder and opening 111 has a circular shape as shown in FIGS. 1 and 2. A circular shape is one possible configuration for the opening because it allows a uniformly tight seal to be formed with a press-fit between the closure portion 140 and the container 110. As shown in FIGS. 1-4, meter 130 may also be generally circular and cylindrical and have a width similar to the width of the container so that the integrated system 100 has an overall generally circular-cylindrical shape that is comfortable to hold and to carry, e.g., in a user's pocket. However, the container 110, meter 130 and opening 111 may be made in any of a number of other shapes. For example, the container may formed as a right oval, elliptical or rectangular cylinder in order to better conform to a user's shirt pocket. Custom shapes are also possible, and the container can be customized with graphical designs appealing to individual users, or the corporate logos of co-branding partners, etc.

As illustrated in FIG. 2, container 110 and closure 140 may also be provided with corresponding flanges 112 and 242, respectively, that fit flush against each other when the closure portion is in the closed position in order to further prevent the infiltration of liquid and vapor. Closure 140 is also illustratively provided with a protrusion 143 which extends beyond the side of container 110 sufficiently aid to the user in opening and closing the container 110, e.g., by pushing upward with the thumb against the protrusion 143. Protrusion 143 may be an extension of the flange 242. Alternatively, protrusion 143 may be formed directly on meter housing 131, as shown in FIG. 3.

Figure 8:
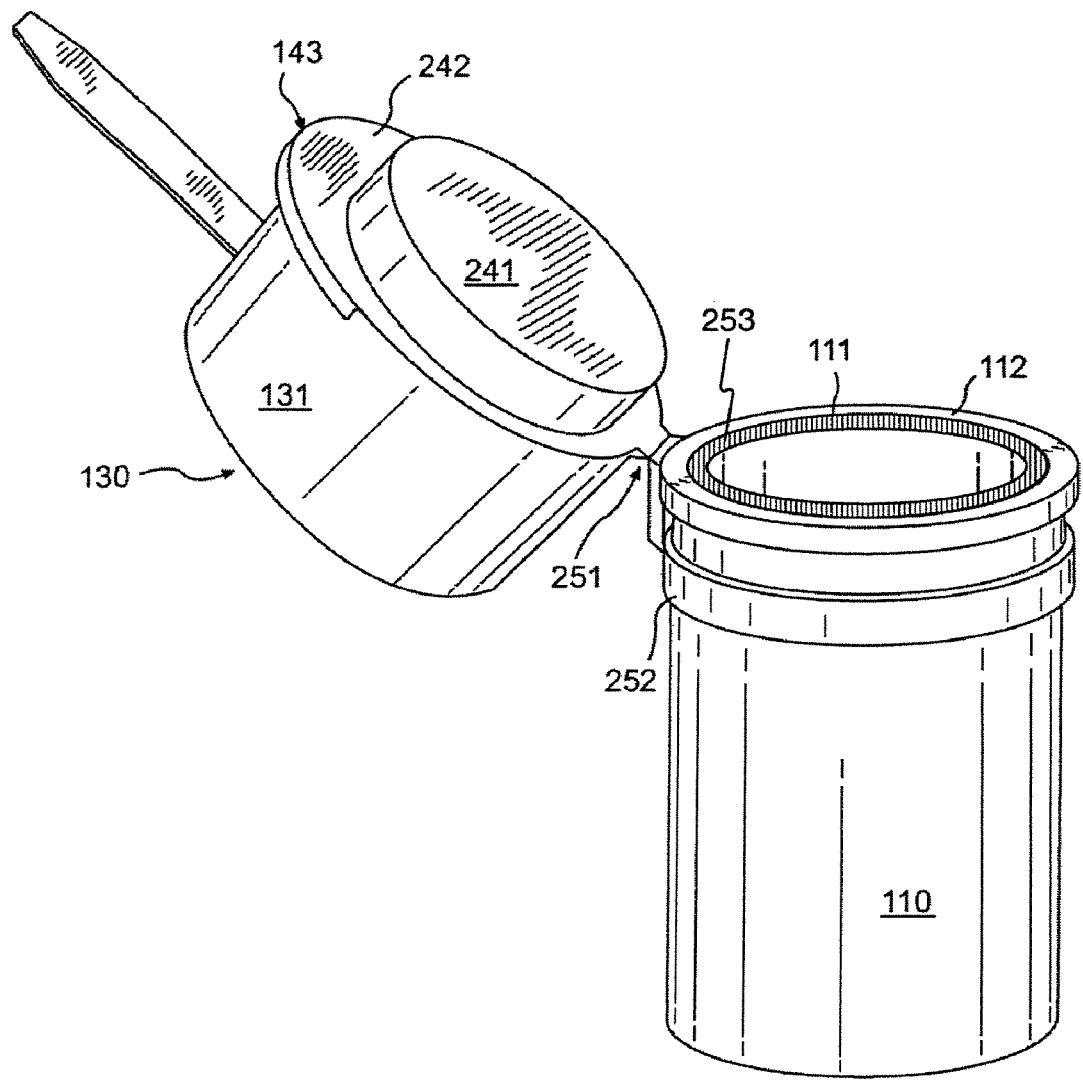
FIG. 8 is a perspective view of a container with a light emitting diode located on the container.
Figure 9:
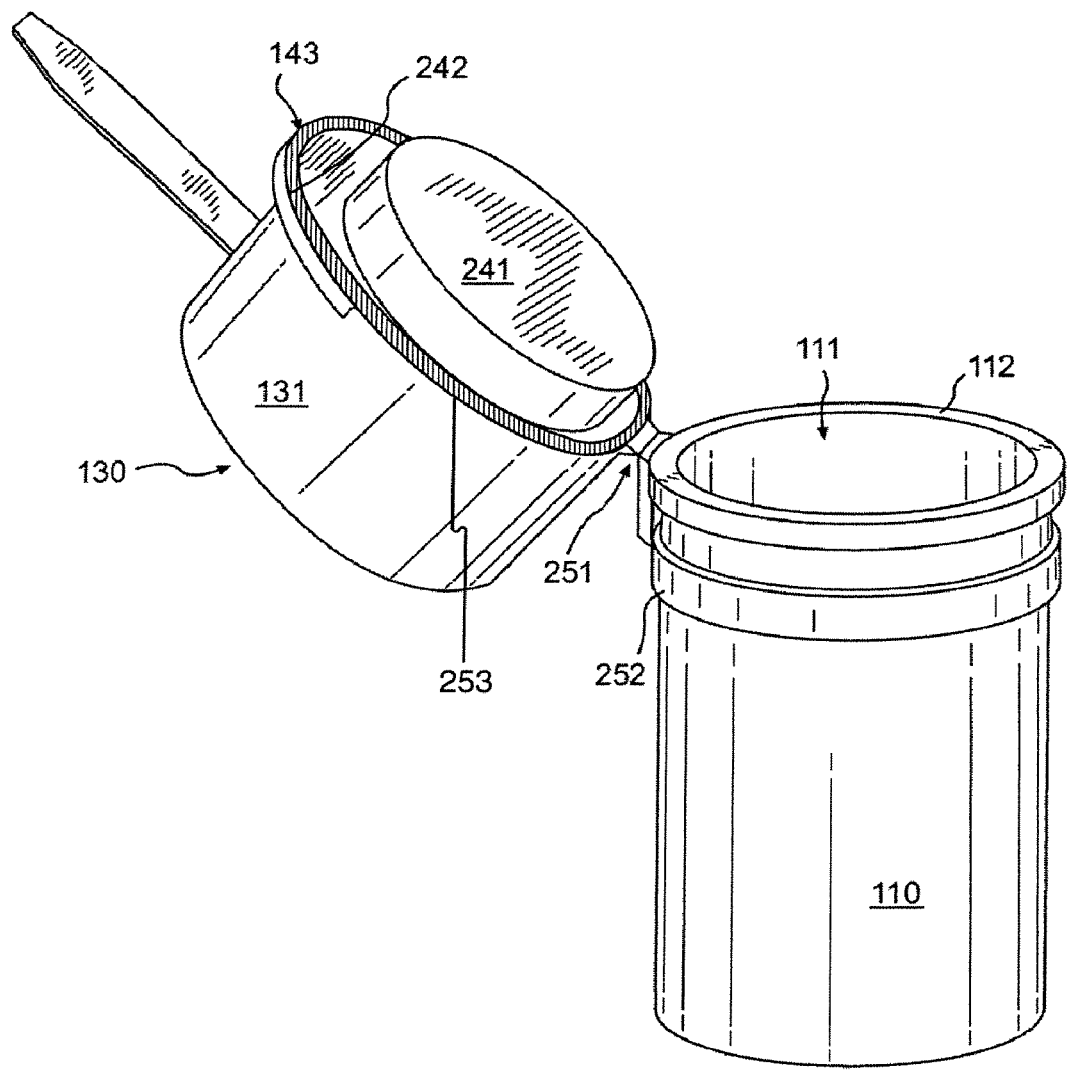
FIG. 9 is a perspective view of a container with a light emitting diode located on the meter.
Figure 10:
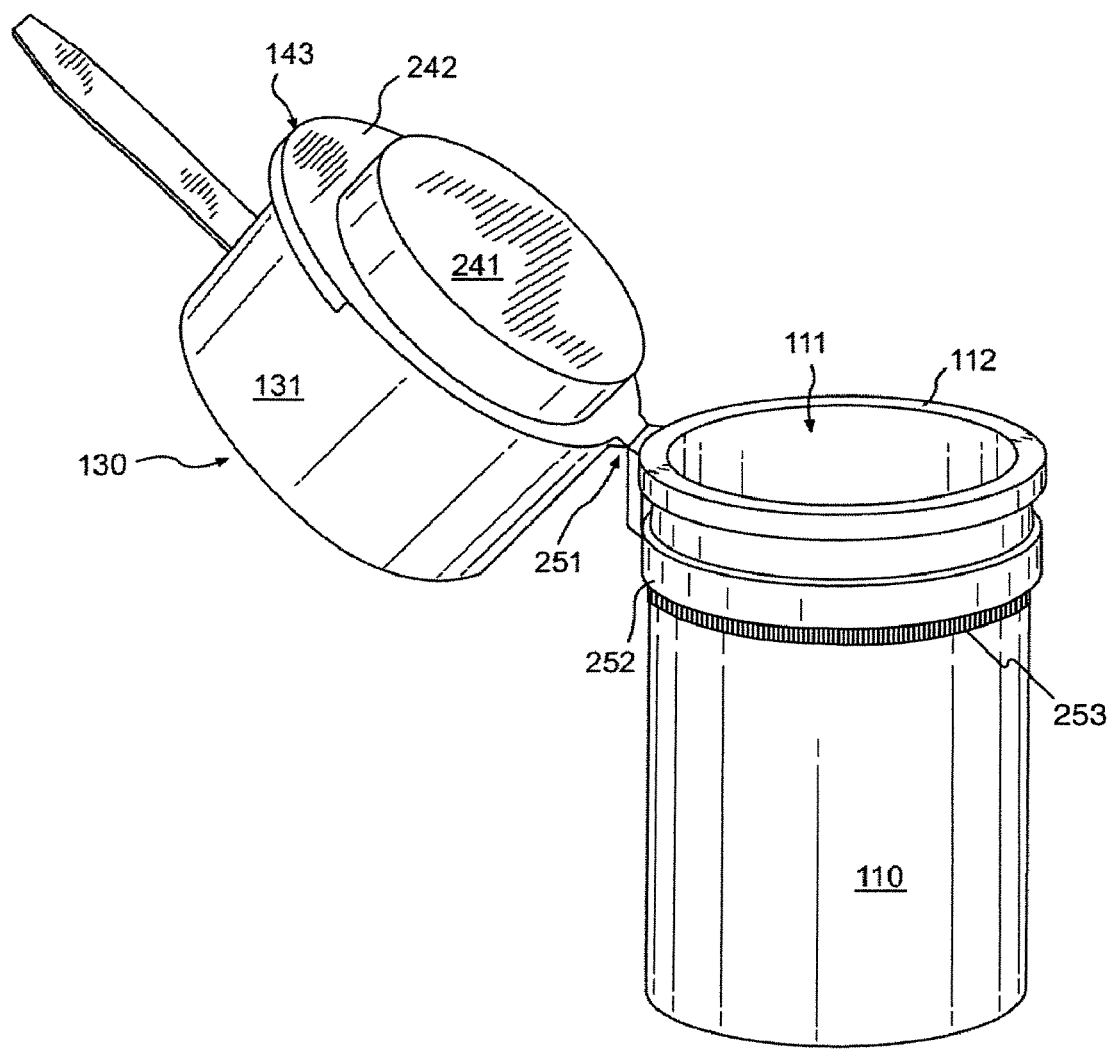
FIG. 10 is a perspective view of a container with a light emitting diode positioned additionally to illuminate an exterior portion of the container.

As shown in FIG. 1, container 110 may be opened by completely removing meter 130 and closure portion 140 from the container 110. Alternatively, meter 130 and/or closure 140 may be connected to container 110 in order to prevent the meter 130 from becoming separated from the container 110 (FIG. 2). Container 110 and meter 130 may be connected by, e.g., a hinge, lanyard or other flexible connector, such as a flexible plastic band or wire, etc. (not shown). In an illustrative embodiment of FIG. 2, a hinge 251 connects the container 110 and the meter housing 131 and/or closure 140. Hinge 251 is positioned such that projection 241 fits within opening 111 in the closed position. The connector (e.g., hinge 251) may have one end connected to the container 110 and the other end connected to the closure 140 and/or meter housing 131. For example, container 110 and closure 140 may be integrally connected by a hinge, as is known in the art. Alternatively, one end of the connector (e.g., hinge 251) may be connected to a ring 252 that is sized to fit over container 110. Ring 252 may be configured to loosely and frictionally engage container 110. As another alternative, ring 252 may be affixed to the container 110, e.g., by welding, gluing, etc. In addition, container 110 may include a light emitting diode (LED) 253 that automatically or selectively illuminates the contents of the container 110 when it is opened. The LED 253 may positioned on the container 110, on the meter housing 131, or positioned additionally to illuminate an exterior portion of the container 110, as illustrated in FIGS. 8-10.

In an exemplary embodiment, container 110 and closure 140 are formed of polypropylene using an injection molding process. However, other materials and processes may be used without departing from the scope of the present invention.

Integrated system 100 may further include a sampling device which the user may use to obtain a sample for testing. The sampling device may be adapted to obtain a biological sample. For instance, the sampling device may include a lancing device that the user can use to draw blood, e.g., for a diagnostic test of blood glucose level.

An exemplary integrated system incorporating a lancing device 360 is shown in FIG. 3. Exemplary lancing device 360 includes a rearward body 312, a finger cover 314, an exterior nozzle 318, an interior nozzle 322 and a trigger 324. Exemplary lancing device 360 further includes an internal spring (not shown) that is used to propel lancet 320 beyond contact surface 321 and through the skin to a depth selected by the user.

Figure 11:
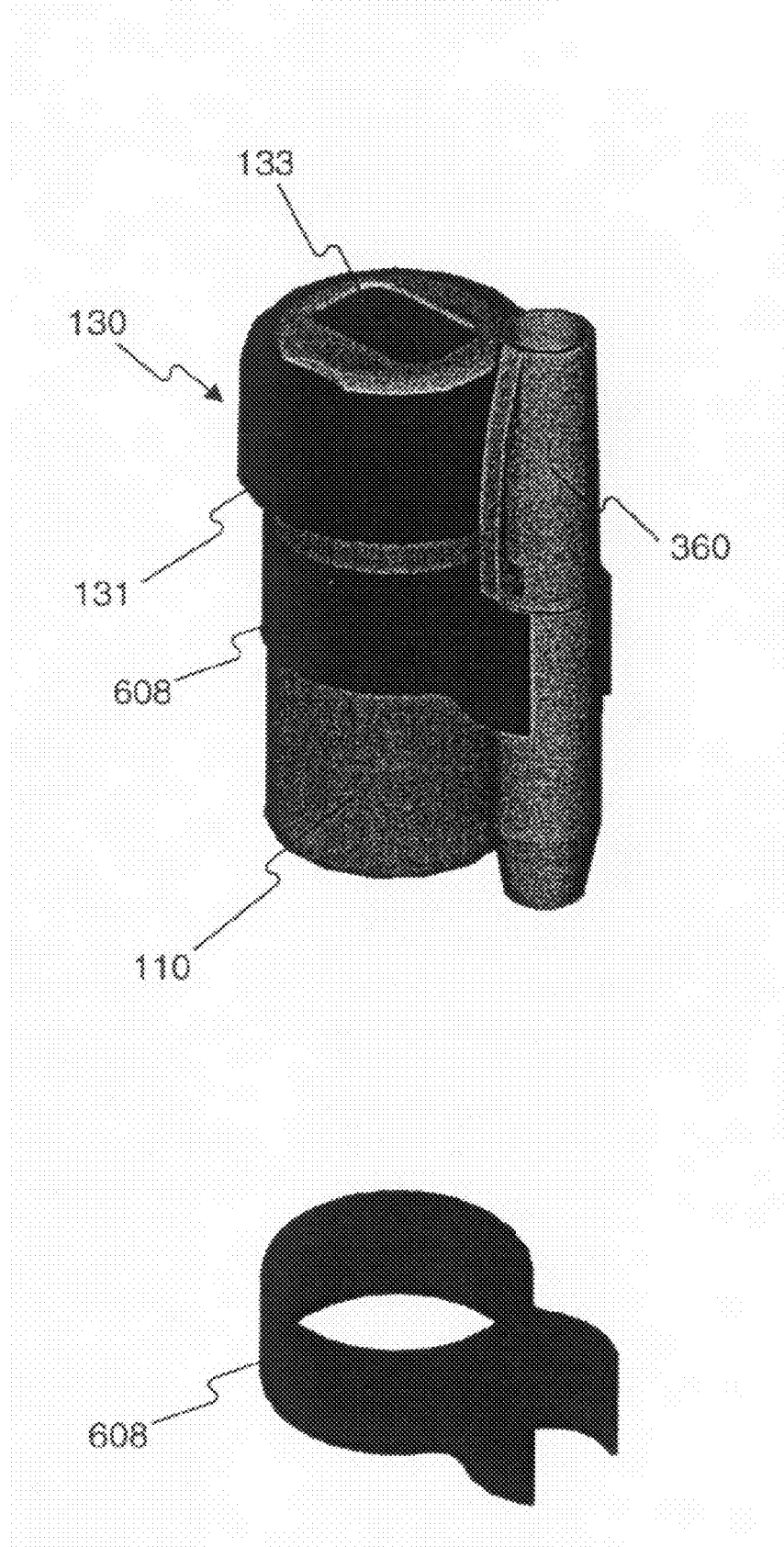
FIG. 11 is a perspective view of a holder in the form of a clip placed around a container.
Figure 12:
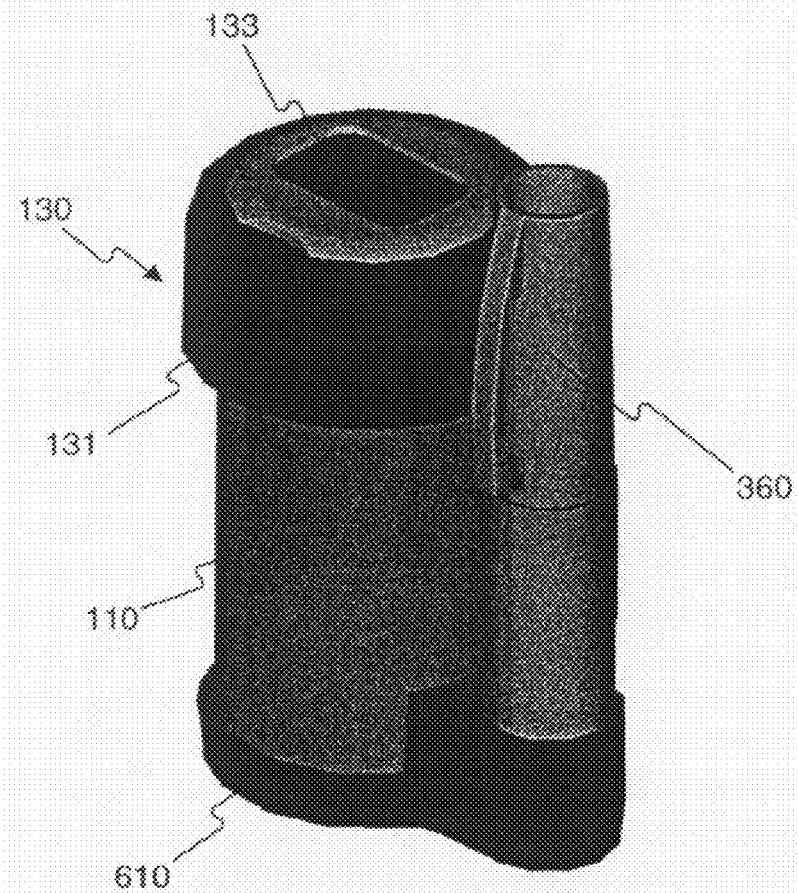
FIG. 12 is a perspective view of a holder in the form of holes used to contain a container and a lancing device.
Figure 12:
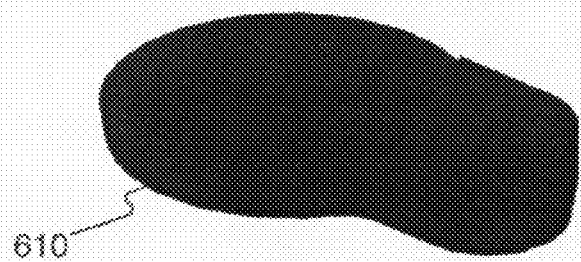

As shown in FIG. 3, the exemplary lancing device 360 is connected to container 110. Lancing device 360 may be permanently connected to the container, for instance, by forming, e.g., rearward body 312, finger cover 314, exterior nozzle 318 or interior nozzle 322 integrally with the container 110, or by bonding one of these components to the container 110, e.g., by a mechanical attachment (clips, brackets, tabs, slots), bonding, gluing, and welding. As would be apparent to one of ordinary skill in the art, other known expedients can be used. Alternatively, lancing device 360 may be releasably connected to the container 110 by providing corresponding releasable connectors on lancing device 360 and container 110. For example, lancing device 360 may be provided with one or more slots, holes, cavities, enclosures, or clips that engage corresponding structures on container 110, or vice versa. As illustrated in FIG. 11, a holder clip 608 can be stretched over container 110 for a snug fit. Holder clip 608 includes a clip that can releasably engage lancing device 360 in place. Similarly, FIG. 12 embodies holder holes 610 designed to engage the container 110 and the lancing device 360 together on one attachment. One having ordinary skill in the art will understand that other types of holders can be used to receive one or more devices used for diagnostic testing, such as brackets, magnets, bayonet locks, slots, tabs, hook and loop fasteners, etc. As further alternatives, lancing device 360 may be connected to housing 131 of meter 130, or to closure portion 140. For instance, only one of the rearward body 312, finger cover 314, exterior nozzle 318 or interior nozzle 322 is connected to the container 110 so that lancing device 360 may be adjusted and used without disconnecting it from the container 110.

In order to draw a sample using exemplary lancing device 360, the user may first select a desired depth of penetration of lancet 320 by rotating exterior nozzle 318 so that the desired depth indicator 326 on exterior nozzle 318 is aligned with arrow 328 on interior nozzle 322. Next, the user loads the internal spring by pulling interior nozzle 322 away from rearward body 312 and places contact surface 321 against the surface to be lanced. The user may then actuate trigger 324 to release the internal spring, which propels lancet 320 beyond contact surface 321 to the indicated depth, and thus into the skin. A blood sample can then be applied to the sample chamber 121 of test strip 120.

Further details of exemplary lancing device 360 are shown in prior application Ser. No. 10/757,776, entitled "LANCING DEVICE," filed Jan. 15, 2004, commonly-assigned with the instant application, which is incorporated by reference herein in its entirety. However, the present invention is not limited to any particular sampling device, and one of skill in the art will recognize that other sampling devices can be incorporated in a manner similar to the exemplary lancing device described above.

2. Prevention of the Use of Incorrect Test Strips

Meter 130 may be calibrated for use with a particular brand or manufacturer's lot of test media by customizing the diagnostic test performed by meter 130 with respect to the particular brand or lot using one or more calibration parameters. These calibration parameters may include environmental corrections (e.g., temperature corrections), timing period corrections (e.g., with respect to incubation time), voltage corrections (e.g., for use in electrochemical tests), color variations (e.g., for use in photometric tests), etc., that customize the diagnostic test function of a controller (not shown) to the particular brand or lot of test media. See, e.g., U.S. Pat. Nos. 6,743,635 and 6,946,299, incorporated by reference above.

Figure 13:
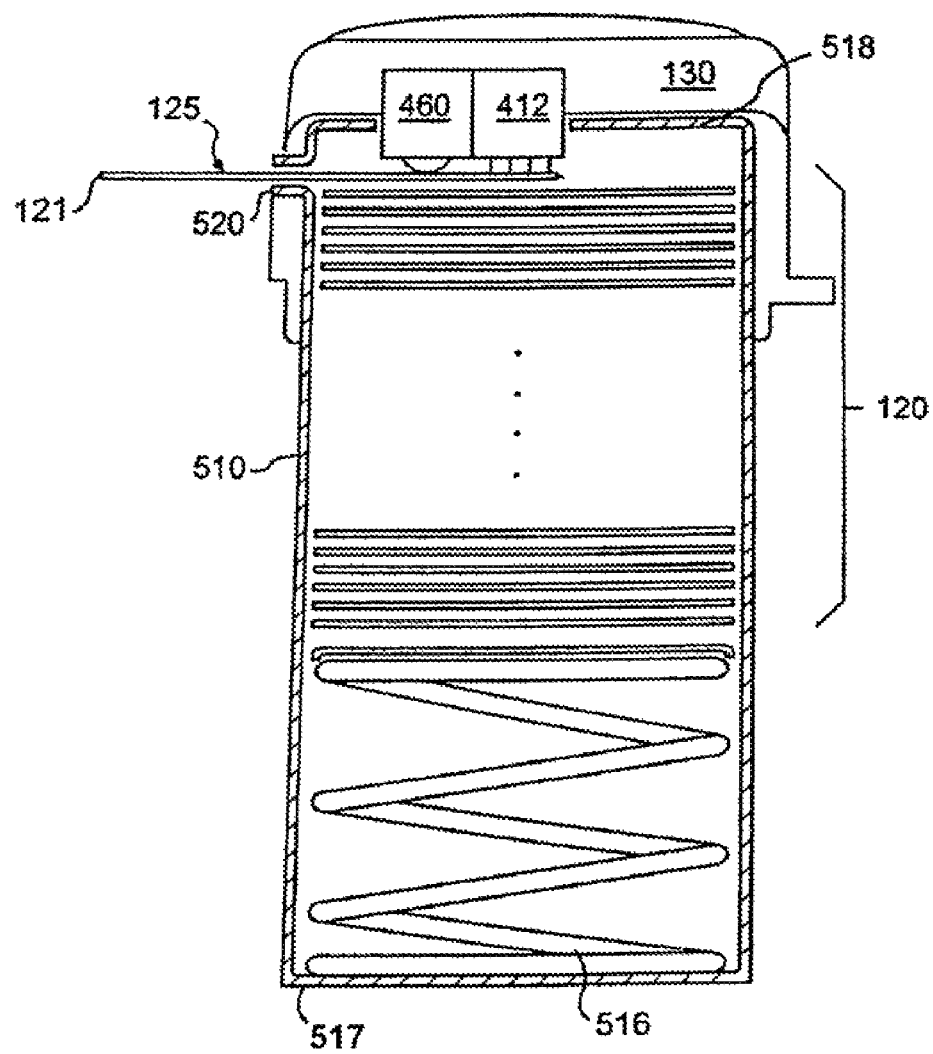
FIG. 13 is a cross-sectional view of a seventh embodiment of an integrated system consistent with the present invention.

In an illustrative embodiment of the present invention, integrated system 100 includes one or more containers 110 or magazines 510 of test strips 120 packaged together with a meter 130 (FIG. 13) to dispense the test strips 120. The test strips 120 in the package are from the same manufacturing lot or otherwise have the same characteristic reaction to blood glucose so that meter 130 may be calibrated once and thereafter used with any of the test strips 120 in the package without recalibration. Magazine 510 may have an interior shape similar to that of the test media in order to maintain the alignment of the stack. For example, for the test strips 120 depicted in FIG. 1, the interior of magazine 510 may be generally rectangular in cross-section. Magazine 510 may include a positioning device arranged on or near a first surface 517 of magazine 510, such as an interior spring 516, which can push the stack of test strips against a second surface, such as the top 518 of magazine 510.

Dispensing mechanism 460, in conjunction with detector 412, may dispense the top test strip 125 in the stack using a linear and/or rotational mechanical action. The mechanical action can be translational or rotational, and may be executed manually (e.g., by the user pulling a slide or rotating a wheel) or by a motor (e.g., a stepper motor) actuated by a user control function. The top test strip 125 is slid from the stack and through slot 520. The test media used with this embodiment may be modified by application of a non-friction coating or film, such as PTFE, to one or both sides in order to ensure smooth ejection.

Figure 28A:
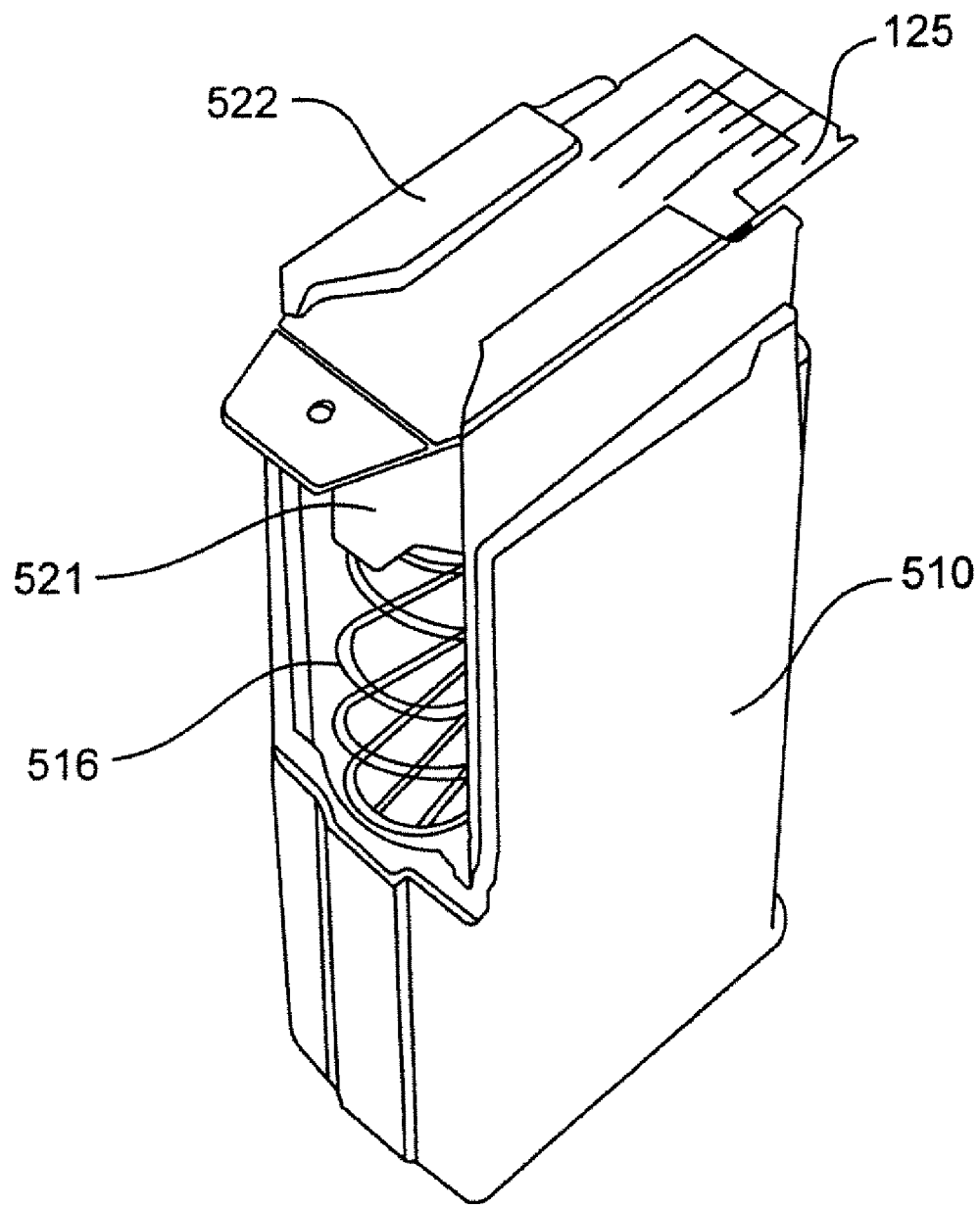
FIG. 28A is a perspective view of an illustrative removable media dispenser.
Figure 28B:
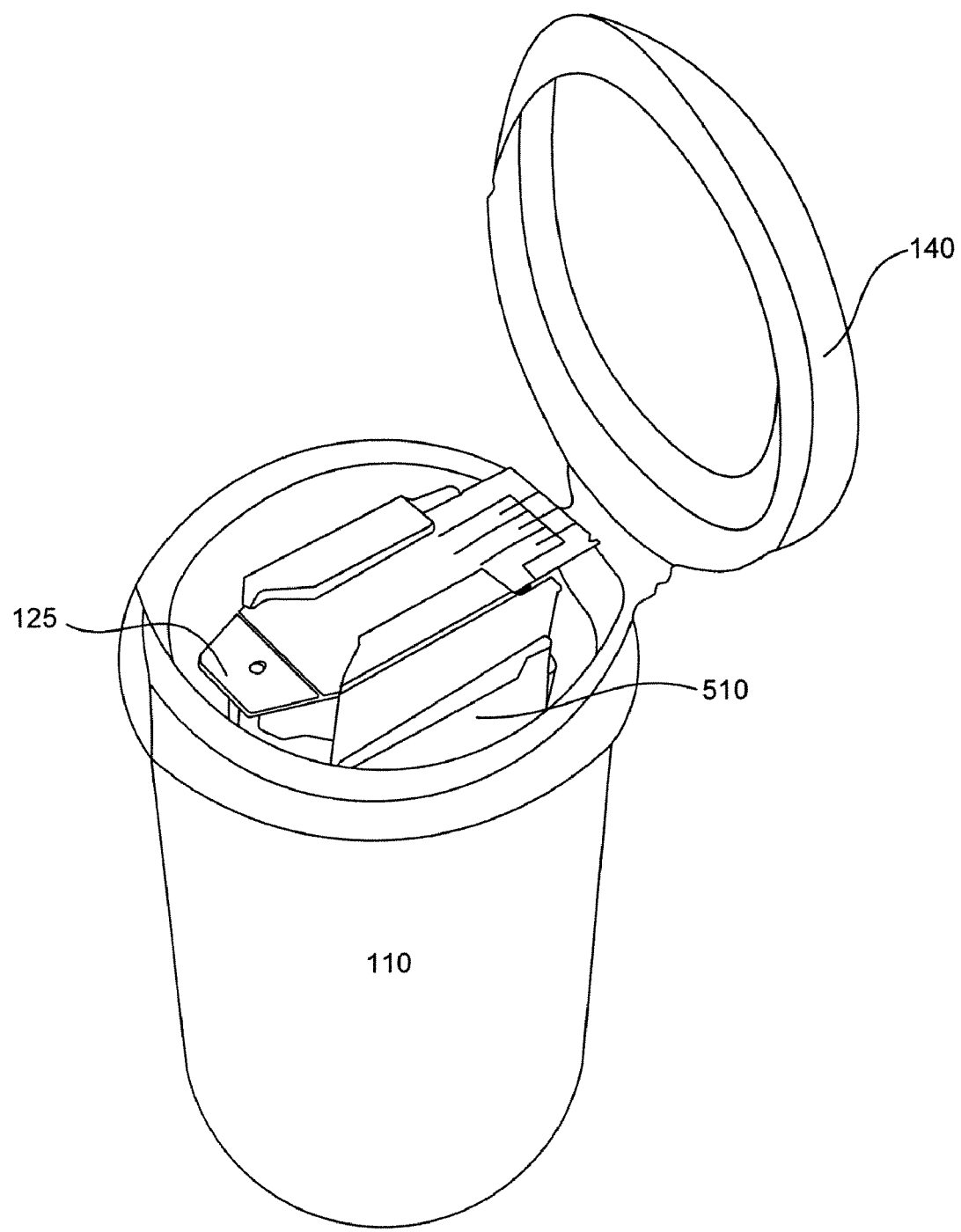
FIG. 28B is a perspective view of an illustrative removable media dispenser contained in an illustrative test strip container.
Figure 28C:
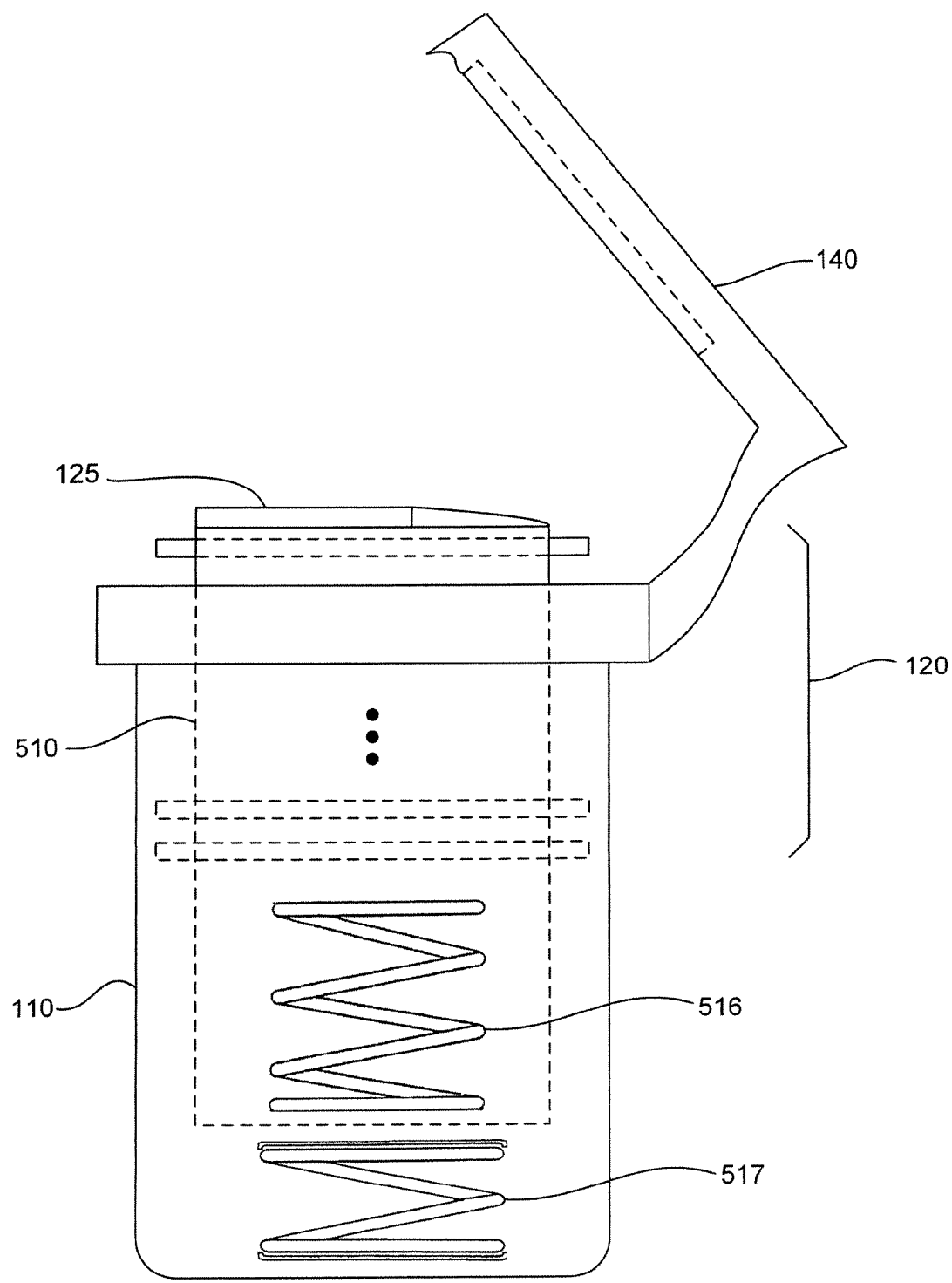
FIG. 28C is a cross-sectional view of an illustrative removable media dispenser contained in an illustrative test strip container.

As illustrated in FIGS. 28A-28C, magazine 510 can also be designed to fit into an existing test strip vial 110 without any modifications to the vial, and may be configured to hold, for example, a vertical stack of at least 50 test strips. Magazine 510 may include a positioning device arranged on or near a first surface of magazine 510, such as an interior spring 516, which can push a support section 521 supporting the test strips toward a retaining section 522 of magazine 510. Alternatively, any other device known in the art as able to push other structures, such as electro-mechanical devices, e.g., a motor-controlled screw, could be used to push the stack of test strips. The retaining section 522 can include a pair of edges substantially perpendicular to lateral walls of magazine 510. The edges can cover all or part of the top section of the magazine 510. Advantageously, the edges only cover part of the top section of the magazine 510 to allow a user to contact the top test strip 125.

The vial 110 may also include an additional spring 517, which can be arranged underneath the magazine 510 and on or near a bottom surface of magazine 510. When magazine 510 is inserted in the vial 110, the spring 517 may be configured to push the magazine 510 toward an opening of the vial so that the top of the stack of test strips protrudes above the edge of the vial when the vial is opened. When the vial is closed, the exterior spring 517 may be compressed to allow magazine 510 to fit within the vial. Alternatively, the vial 110 may not have any additional spring, and the vial 110 may then include a closing portion 140, which may itself be a portion of the meter 130, having a suitable cavity so that the magazine 510 can rest on the bottom of vial and protrude from the vial when the vial is opened without having to move the magazine 510. One or more coding elements may also be added onto the magazine 510 or onto each of the test strips 120.

The diagnostic test function of the packaged meter 130 may be precalibrated by the manufacturer or distributor, e.g., by providing instructions and/or data customized to the associated test media. Alternatively, meter 130 may be calibrated at the user level by requiring the user to calibrate the meter with respect to a particular brand or lot of test media prior to using the meter to conduct diagnostic tests. For example, the user may utilize user control or input/output functions to enter or download calibration data or a code from which a controller (not shown) may derive calibration data. In another approach, each test media container 110 (or a co-packaged group of containers from the same lot) may be provided with a data storage device that stores the calibration data electronically. See, e.g., U.S. Pat. Nos. 6,743,635 and 6,946,299, incorporated by reference above.

In the event the test strips 120 in the package are not from the same manufacturing lot or otherwise do not have the same characteristic reaction to blood glucose, users may forget to calibrate the meter 130 for use with a new brand or lot of test media. Accordingly, the present invention allows the meter 130 to be removed from the test strip container 110 and transferred to another container by using several different coding techniques that prevent erroneous results that could have serious consequences for the user if the meter 130 is incorrectly calibrated. As long as the meter is properly associated with a coding container for strips of a matched lot, the user does not need to take further action to program the meter. One having ordinary skill in the art will understand that the different coding techniques and coding elements may be used to provide a variety of diagnostic tests, with each diagnostic test testing a distinctive analyte in a sample.

In one illustrative embodiment, common coding errors associated with use of an old code chip or button code are prevented by the method of on-container coding. On-container coding techniques allow a larger range of code numbers to be encoded due to large space available on the top, bottom, and side portions of container 110. The meter 130 is keyed to align with the container 110 such that it lines up with the code placement in order for the container 110 to be read accurately. The container can also be pre-read prior to insertion in the meter. This method is non-technique dependent or evident to the user, eliminating common coding errors associated with forgetting to change the code chip or button code on older technologies. Strips are unlikely to be mixed among different containers due to container strip lot code association. The meter can be programmed not to perform a test unless a code is properly accessed by the meter beforehand.

Figure 14:
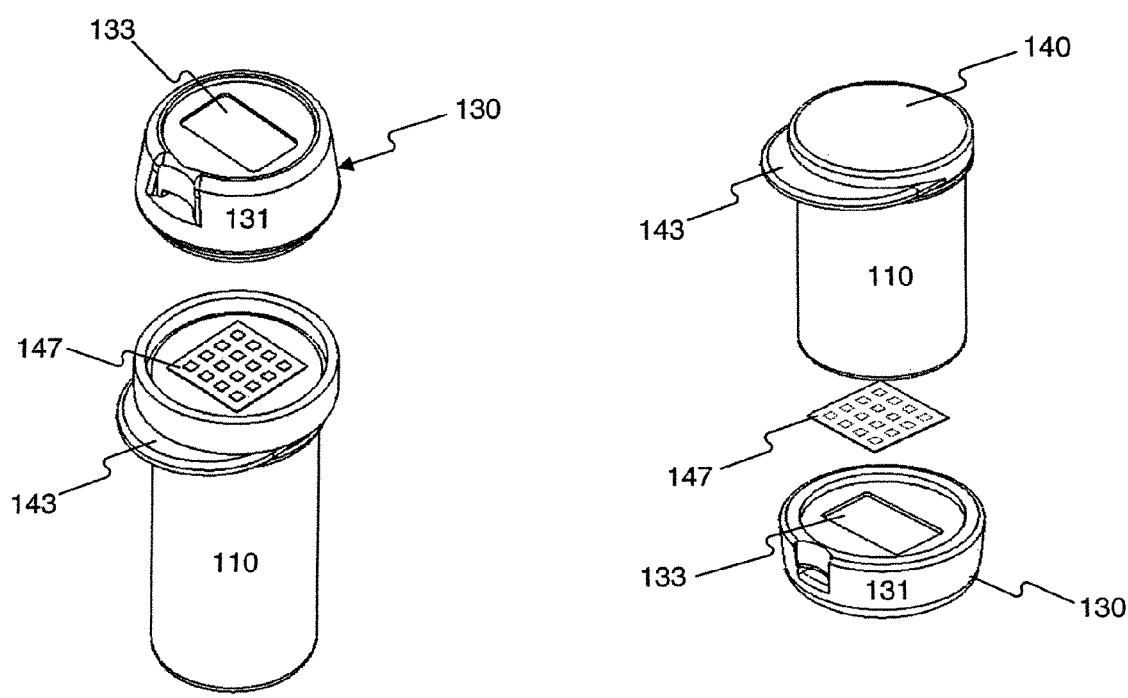
FIG. 14 is a perspective view of a conductive coding pattern attached to a test strip container with a removable meter.
Figure 15:
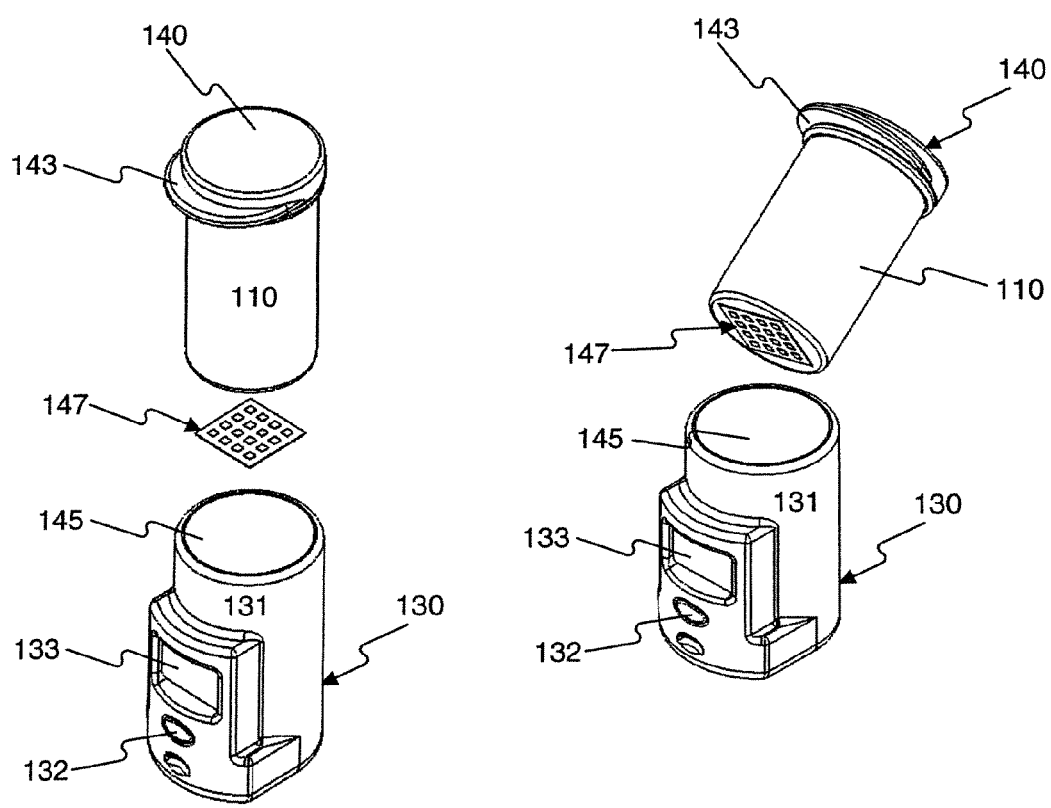
FIG. 15 is a perspective view of a conductive coding pattern attached to a test strip container inserted into a meter receptacle.

As illustrated in FIGS. 14 and 15, the on-container coding method includes an electrically conductive coding pattern placed on a substrate 147 and directly printed on the test strip container 110 or attached to the container 110 with an adhesive label, such that the meter 130 makes contact with the coding pattern when attached. The meter 130 then reads selected electrical properties, e.g., resistance values, of the coding pattern. The electrical values are associated with a proper code group stored in the meter 130 for that particular test strip lot. When the coding pattern placed on substrate 147 is replaced with a new coding pattern, the user need only attach the container to the meter to recalibrate the meter with the new coding values, as described in the method above.

The integrated system 100 is designed such that container 110 can be used with a removable meter 130 or container 110 may be inserted into receptacle 145 of meter housing 131 in a keyed locating position, as described above in FIGS. 5 and 6. The on-container coding method is advantageous in that it can be applied to the test container 110 after manufacturing has fully packaged the test strips 120 in the containers 110. One having ordinary skill in the art will understand that other information can also be encoded on container 110 such as product type, test type, etc.

Figure 16:
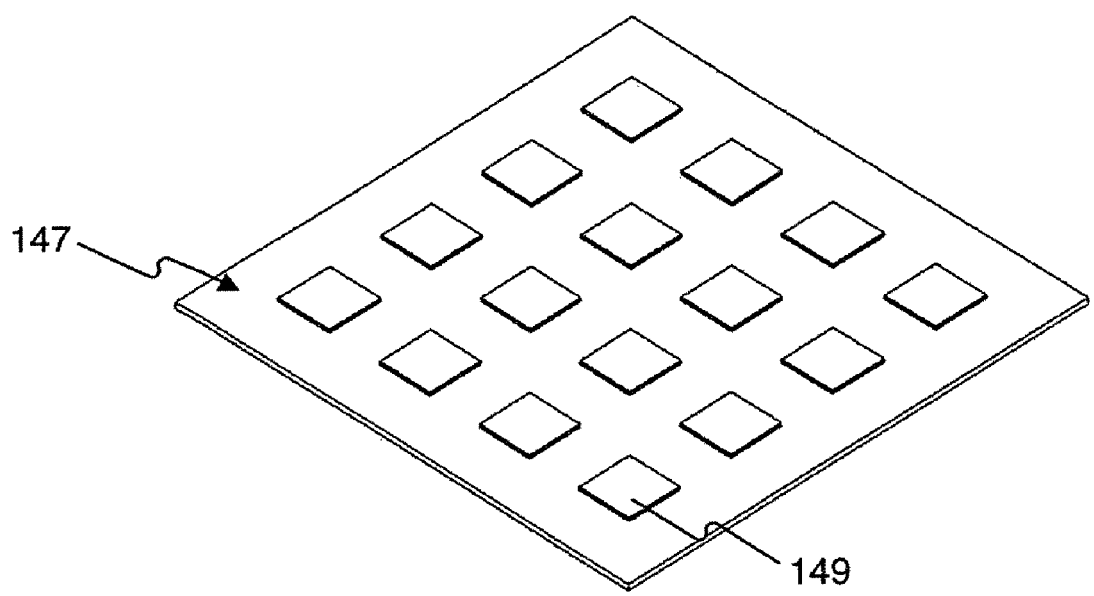
FIG. 16 is a perspective view of a substrate with several coded contact pads.

The information that is stored on the container 110 can be as complex as an entire set of parameters for lot calibration or as simple as a lot code index that is correlated to a lot calibration pre-programmed in the meter 130. As illustrated in FIG. 16, a substrate 147 includes a coding pattern with sixteen contact pads 149 or coding bits, giving the possibility of selecting $2 \times 10^{16}$ (65535) coding numbers or sixteen bits of information. The code conductor may either be exposed or removed from substrate 147, or a printed electrical insulation pattern can cover the conductive substrate to produce opened, closed, or resistive encoding. When one contact pad 149 is used as a common coding bit, only $2 \times 10^{15}$ (32768) codes are generated, but only one contact per coding pad 149 is required, therefore, more information may be stored. However, since individual pads 149 without a common coding bit require two contacts to make up the coding bit, a reduced number of codes are available. As one having ordinary skill in the art will understand, the more codes that can be generated and selected, the greater the flexibility in configuring the system. The coding scheme can be similar to that described for on-strip coding in copending U.S. patent application Ser. No. 11/181,778 filed on Jul. 15, 2005, and commonly assigned with the present application, the contents of which are incorporated herein by reference.

Figure 17:
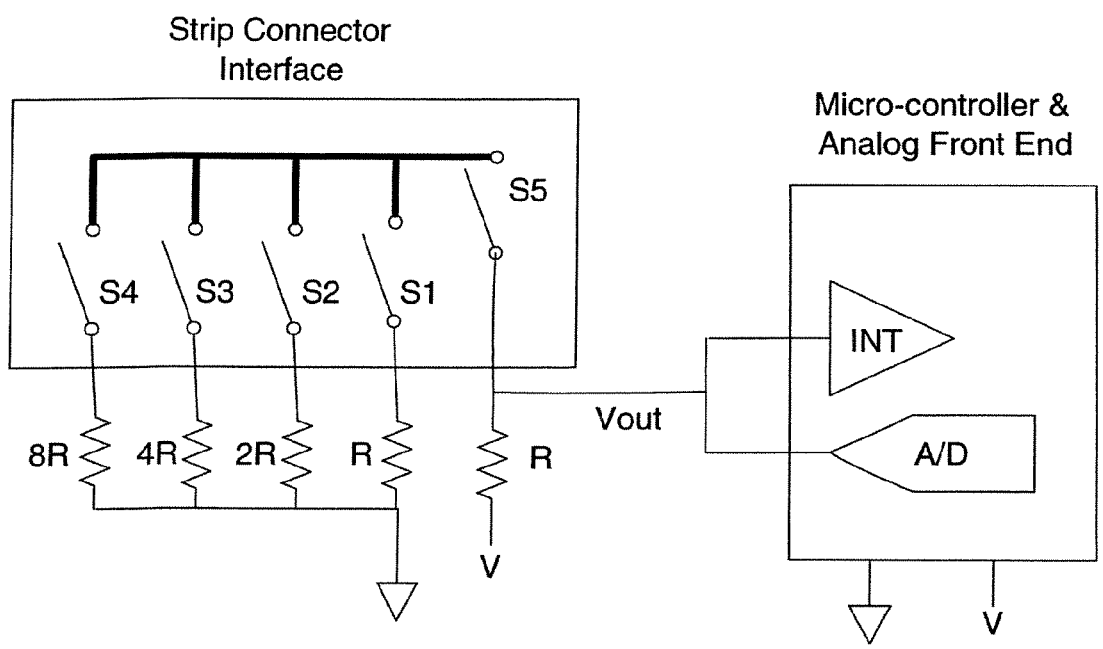
FIG. 17 is a perspective view of an analog code interface with a negative level trigger wake-up.
Figure 18:
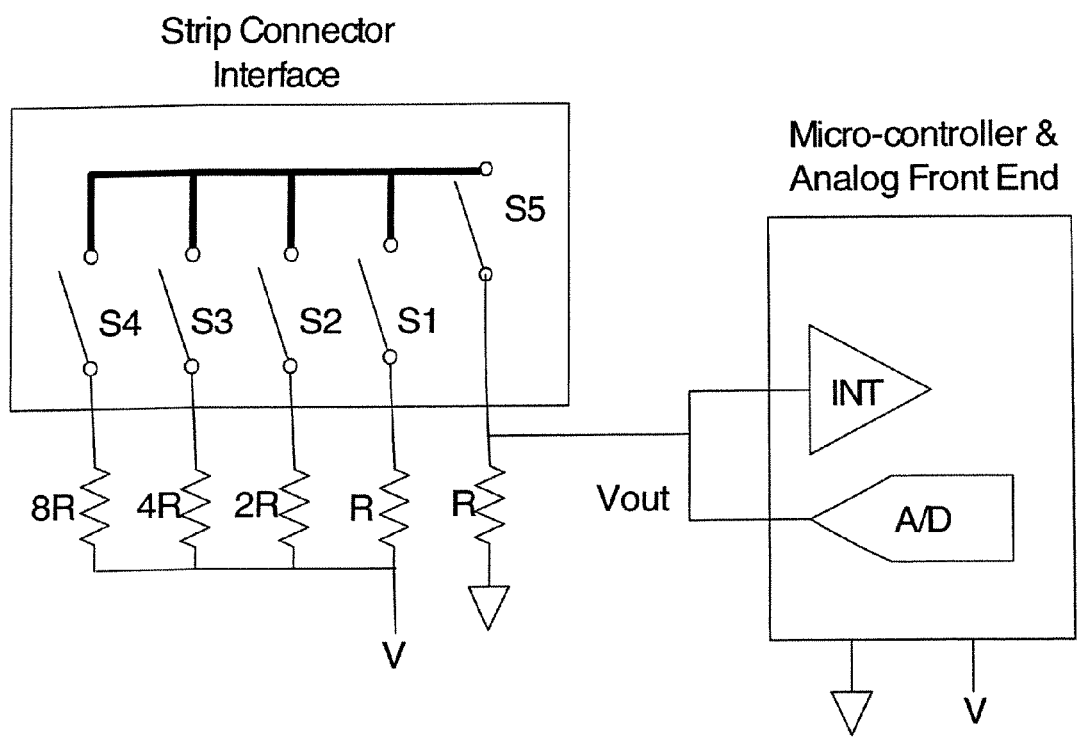
FIG. 18 is a perspective view of an analog code interface with a positive level trigger wake-up.

The interface to the coded contact pads 149 can either be resistive and read in an analog style or digital and read as on or off switch closures. With analog resistive on-container coding, when the container 110 comes in contact with meter 130, the meter 130 reads the resistance value patterns to select the proper code group in the meter 130 for that particular test strip lot. The analog method requires a preset resistive ladder (R, 2R, 4R, 8R), as illustrated in FIGS. 17 and 18, to be interconnected to the contact pads 149 such that permutations of printed non-conductive ink can be correlated to distinct lot code information using a voltage drop, resistance or current measurement. Resistors can also be printed in different values and read in a similar arrangement. The analog method also can be simultaneously used as the auto-on feature so long as each code has at least one contact pad 149 free of non-conductive ink, which can make a low impedance connection to wake-up meter 130. FIGS. 17 and 18 illustrate an analog code interface with a negative and positive level trigger wake-up, respectively. The analog voltage, resistance or current level may also be used to identify the test type, simulate a test, check the test strips 120, or check the manufacturing tests being employed.

Figure 19:
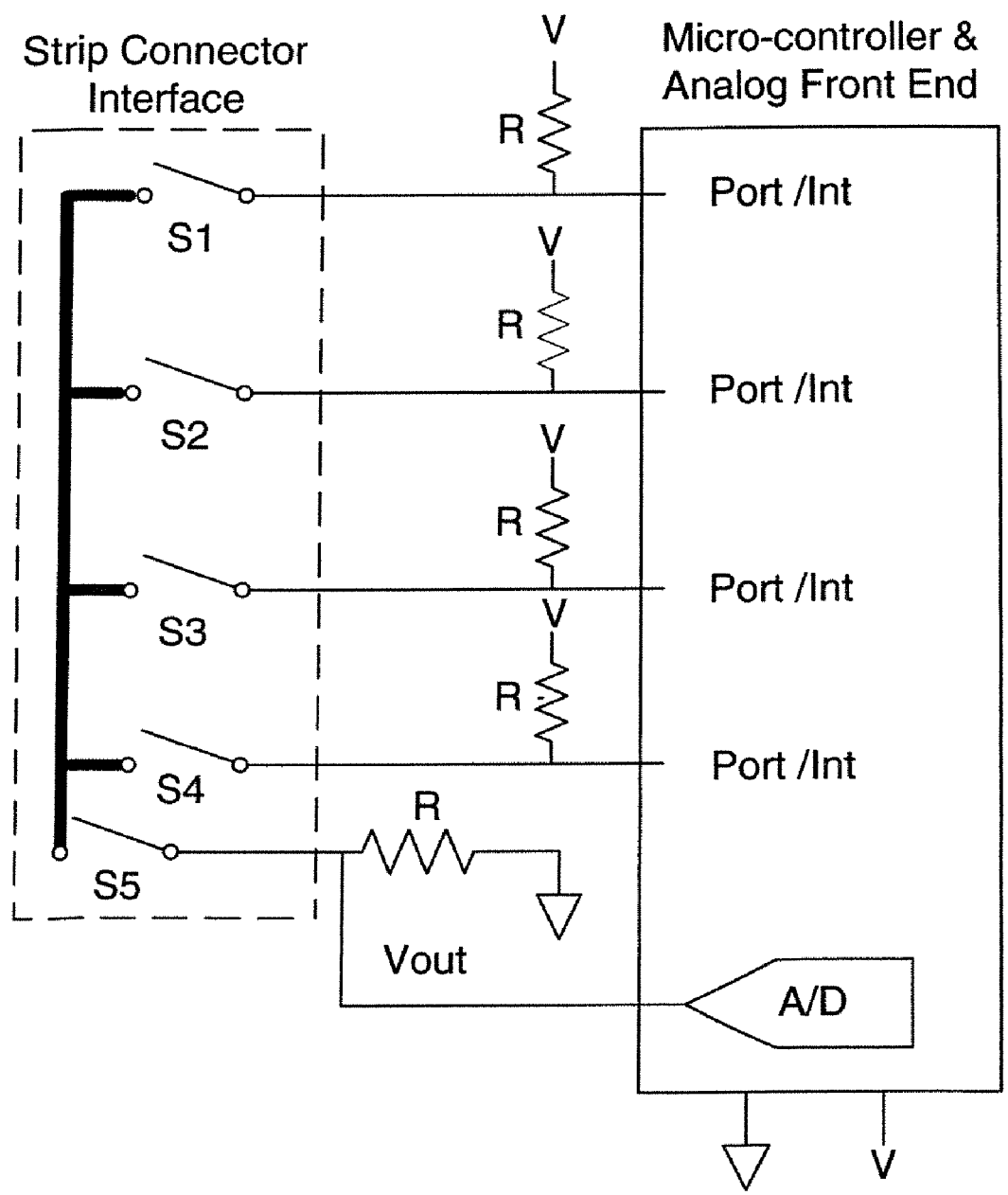
FIG. 19 is a perspective view of a digital code contact pad meter interface.

With digital conductive switch on-container coding, a binary coded number is encoded using the patterned conducts as switches to open or close a switch to represent a 1 or 0 value in the lot code. Similar to analog resistive coding, in digital conductive coding the coding pattern can be preprinted and attached to the container 110 or printed on the container 110 directly. As shown in FIG. 19, a code contact pad meter interface includes a microcontroller and analog front end with interrupts (int) and an A/D converter, a plurality of resistors (R), and a strip connector interface with a plurality of switches (S1, S2, S3, S4, and S5). When the container 110 is placed in contact with the meter 130, meter 130 is turned-on via the plurality of interrupts, having at least one contact switch closed.

The digital method requires each contact pad 149 to be read as individual inputs, unlike the single input required by the analog method. For the digital method to be simultaneously used as an auto-on feature, the inputs need to be wired together or connected to the interrupts of the microcontroller. Each code must have at least one contact pad 149 free of non-conductive ink such that a low impedance connection can be made to wake-up the microcontroller. Alternatively, one contact pad 149 can be dedicated solely to wake-up the meter 130 and indicate whether the test strip 120 or code print is in the correct position.

As described above, non-conductive ink with levels of high and low impedance produces a binary code, yielding a code index based on the number of contact pads 149 implemented, where the number of codes is $N=2^P$ and P is the number of contact pads 149. When the digital on-container coding method is integrated with the auto-on feature, the number of codes that can be generated is reduced to $N=2^{P-1}$. As a test strip 120 is inserted into meter 130, one contact switch is closed and the meter 130 wakes up by pulling the microcontroller's interrupt either high or low. The meter 130 then checks the voltage out ($V_{out}$) to determine the test type and reads the code bits to determine the code value. A code number or code status is displayed on the liquid crystal display (LCD) 133 of the meter 130 for a moment before the meter goes back to sleep. The code value selected by the meter 130 is associated to a stored set of coefficients in the meter's memory for use in test configuration. This code can also be associated with other types of strip parameter information, i.e. code integrity, meter type, correct alignment position of the test strip container 110 with meter 130, manufacturing meter quality control (QC) tests, etc. Manufacturing meter QC tests can be identified by insertion of an additional fixed resistor in the code circuit, instead of the normal resistance of the code conductor, to identify a special test. Additionally, the voltage drop across the plurality of resistors (R) may be used to check whether contact resistance is valid or can be used in a resistive coding representation. For example, after the container 110 is placed in contact with meter 130, meter 130 reads the contact resistance from the resistive contact pads 149 with the A/D converter to encode strip lot code information.

Alternatively or in addition, the on-container coding method includes a coded memory chip 151 embedded or attached to the test strip container 110. The coded chip can be an electrically erasable programmable read-only memory (EEPROM). Embedding the memory chip 151 into container 110 permits storing the largest amount of information possible related to the strip lot coding parameters. The memory chip 151 can be mounted to a printed circuit board (PCB) 153, which is attached to the top, bottom, or side portions of the test strip container 110. Data is then read and transferred into the meter's memory (not shown) after the PCB 153 is inserted or attached to meter 130, such that mechanical connecting contacts 155 on the meter 130 make contact with the PCB 153 and EEPROM chip 151. Coded memory chips 151 are monetarily advantageous in that the more expensive meter component 130 may be reused many times, whereas the less expensive coded memory chip 151 can be discarded with the used test strip container 110 after use. Additionally, test strips 120 will not be mixed among different containers due to container strip lot code association. The embedded EEPROM memory chip 151 can also be disabled when a preset number of tests are completed. One having ordinary skill in the art will understand that many other stored parameters may disable memory chip 151, i.e. strip specific test parameters, manufacture, test type, etc.

Figure 20:
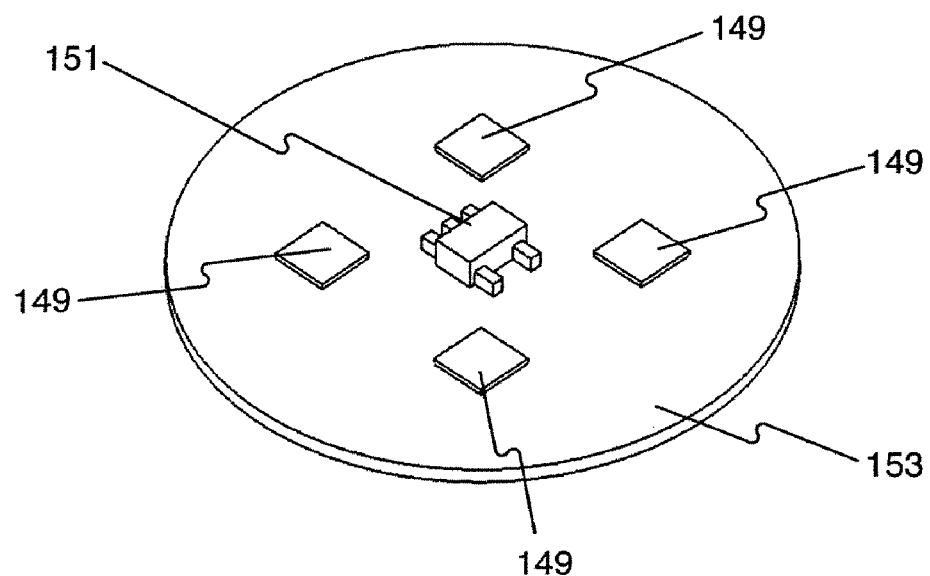
FIG. 20 is a top and bottom view of a memory chip on a printed circuit board with contact pads.
Figure 20:
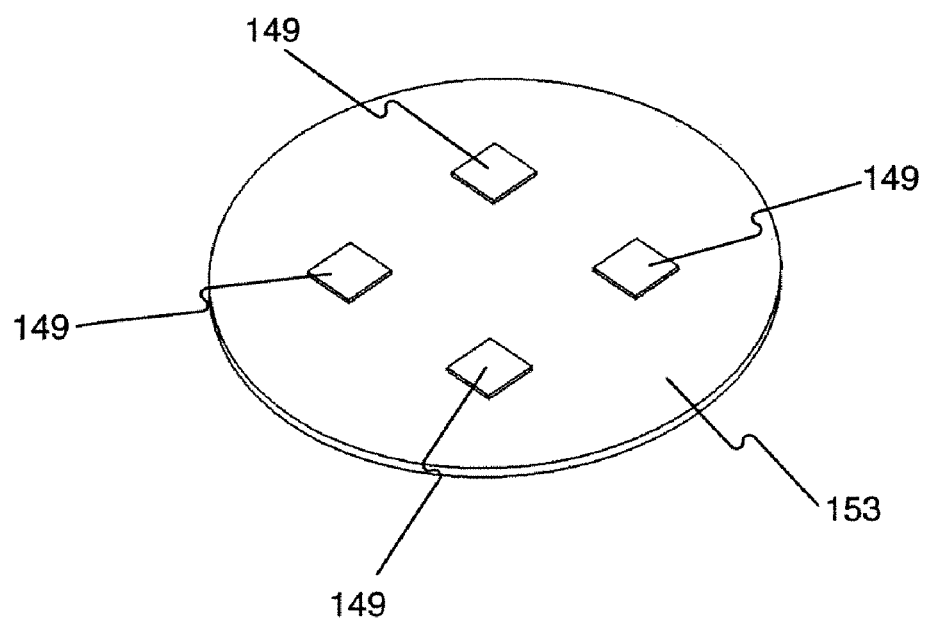
Figure 21:
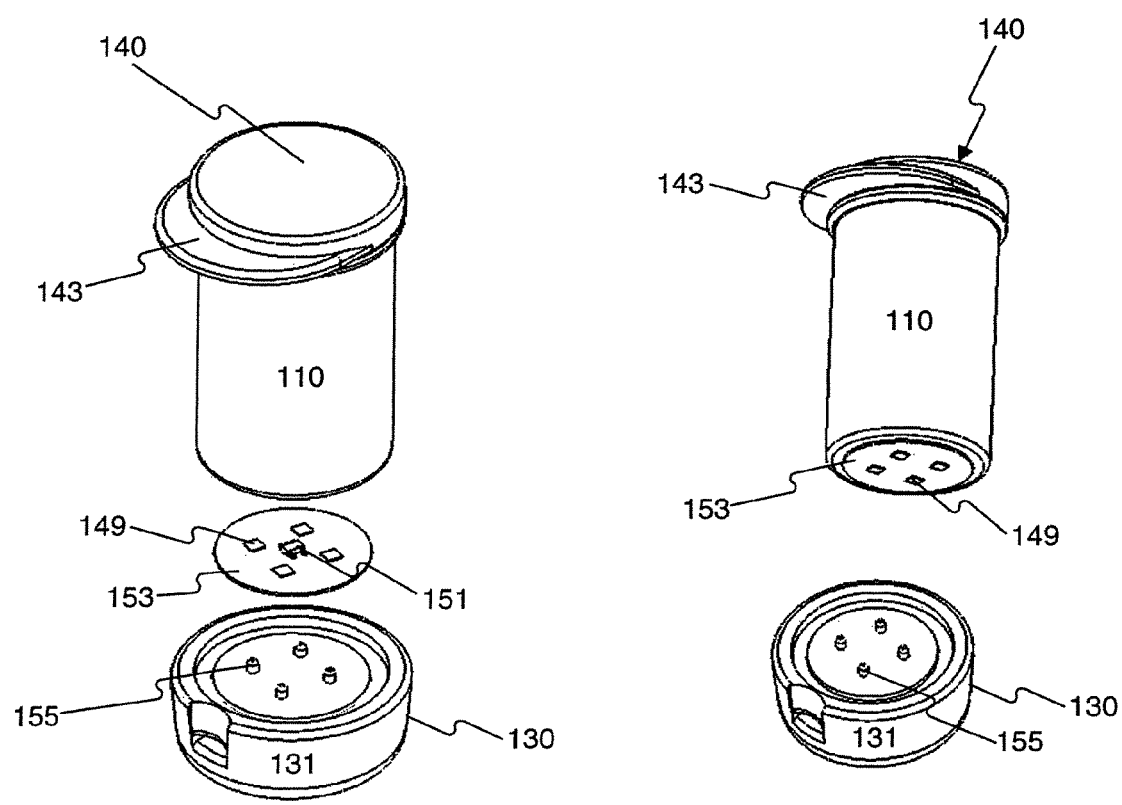
FIG. 21 is a perspective view of a memory chip on a printed circuit board with contact pads and a removable meter attached to a bottom portion of a test strip container.
Figure 22:
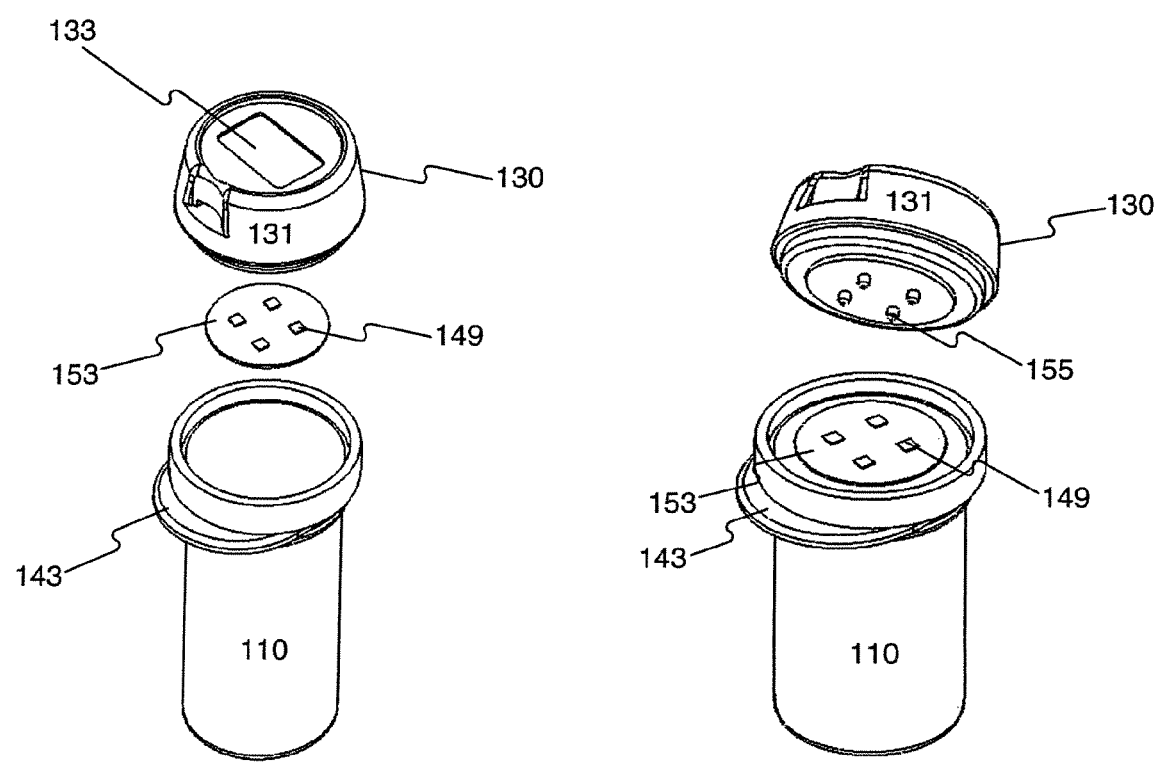
FIG. 22 is a perspective view of a memory chip on a printed circuit board with contact pads and a removable meter attached to a top portion of a test strip container.
Figure 23:
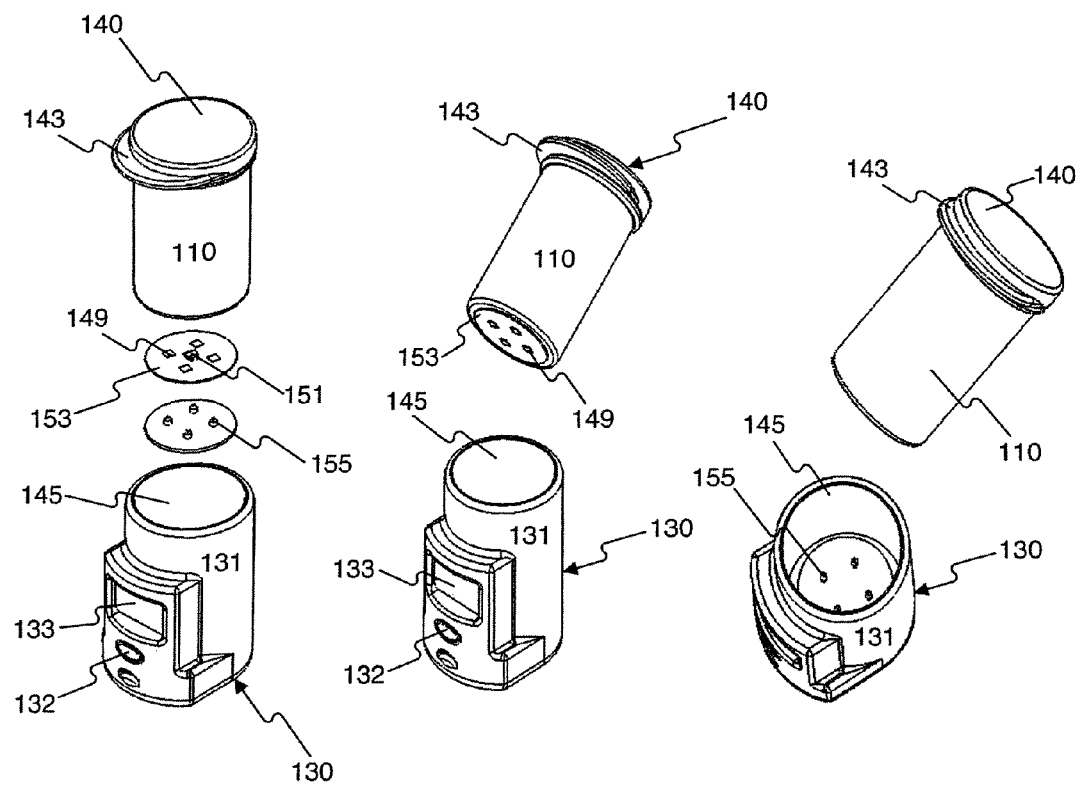
FIG. 23 is a perspective view of a memory chip on a printed circuit board with contact pads attached to a bottom portion of a test strip container inserted into a meter receptacle.

As illustrated in FIGS. 20-23, memory chip 151 is mounted on PCB 153 with contact pads 149 for transferring or storing lot code information on each test strip container 110. Removable meter 130 and PCB 153 with the coding information may be attached to the top or bottom portions of container 110 (FIGS. 20-22). Alternatively, PCB 153 can be attached to a bottom portion of the container 110, which is then inserted into the receptacle 145 of meter housing 131 in a keyed locating position, as described above in FIGS. 5 and 6 and shown in FIG. 23.

Figure 24:
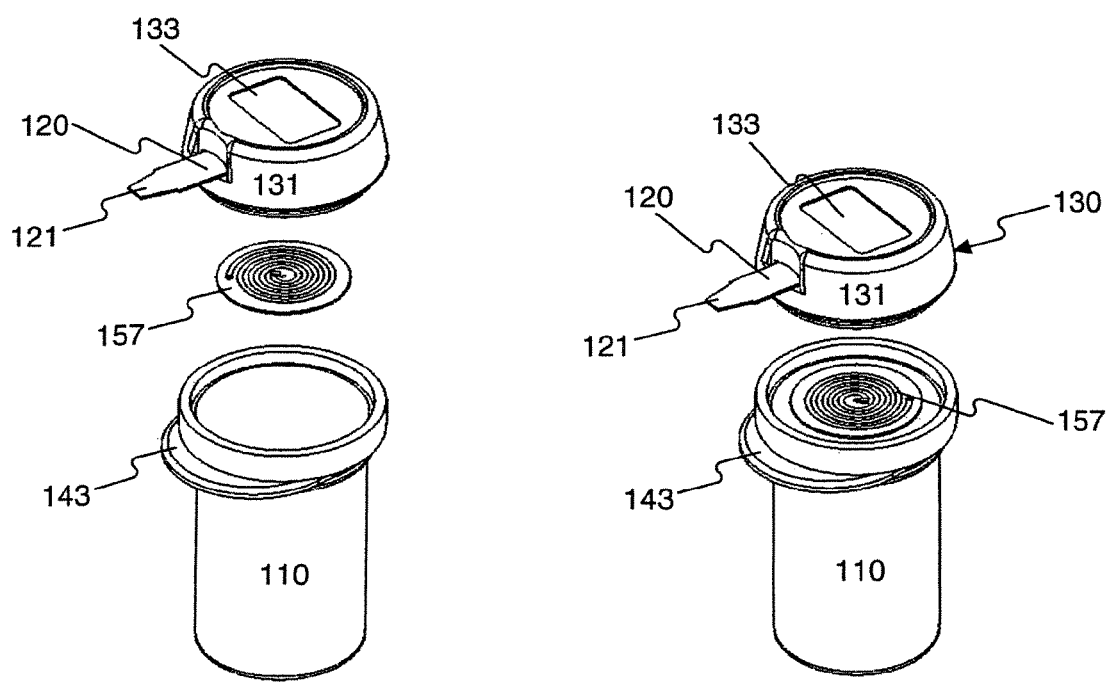
FIG. 24 is a perspective view of a radio frequency identification tag in close proximity to a removable meter and attached to a top portion of a test strip container.
Figure 25:
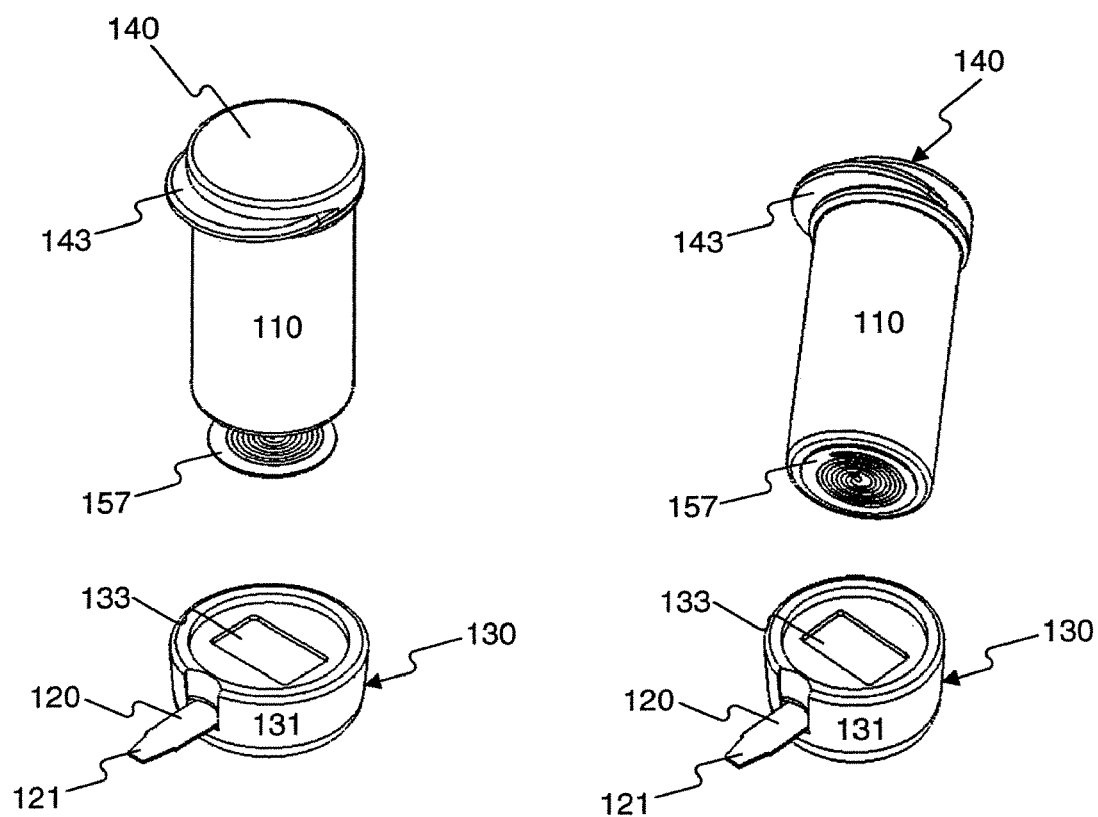
FIG. 25 is a perspective view of a radio frequency identification tag in close proximity to a removable meter and attached to a bottom portion of a test strip container.
Figure 26:
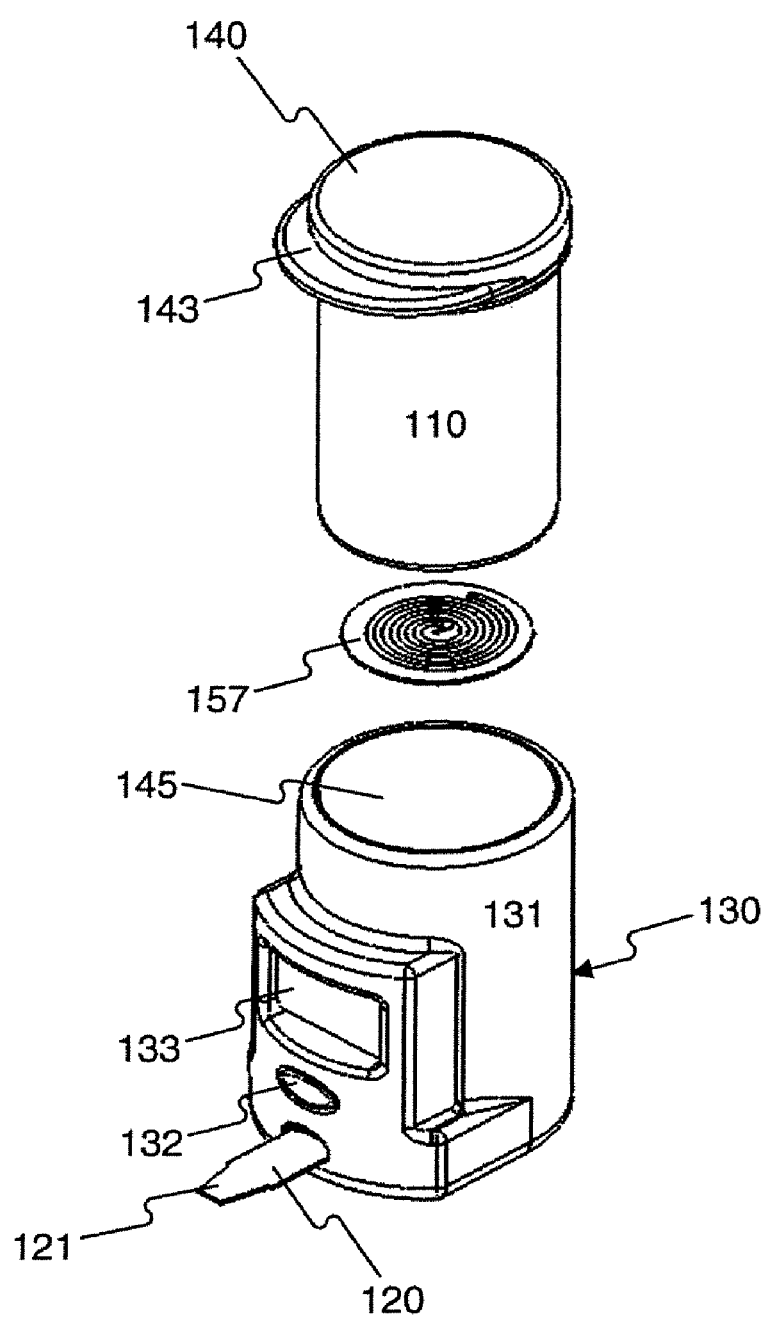
FIG. 26 is a perspective view of a radio frequency identification tag in close proximity to a meter and attached to a bottom portion of a test strip container inserted into a meter receptacle.

In another illustrative embodiment, the on-container coding method may include a radio frequency (RF) device 157, such as a RF identification tag (RF ID tag) code or other near field communication (NFC) device, that contains lot calibration information. The RF device 157 can be embedded into the test strip container 110 itself or be applied as an RF label to the top, bottom, or side portions of container 110. As illustrated in FIGS. 24-26, RF ID tag 157 is shown in close proximity, approximately 0 to 1 mm, from meter 130 for coding the meter 130 with lot specific information. Removable meter 130 and RF ID tag 157 with the coding information may be attached to the top or bottom portions of container 110 (FIGS. 24 and 25). Alternatively, the RF ID tag 157 can be attached to the bottom portion of the container 110, which is then inserted into the receptacle 145 of meter housing 131 in a keyed locating position, as described above in FIGS. 5 and 6 and shown in FIG. 26.

During production of the RF device 157, the lot calibration information is wirelessly programmed into the device. When the wireless container 110 is placed in close proximity to the reading, writing, or powering antenna in the meter 130, i.e. approximately 0 to 1 mm in distance, the RF device 157 allows the meter 130 to read the lot information from the container 110 wirelessly, eliminating the need for the user to code the meter 130. It is important for the RF device 157 to be in close proximity to the meter 130 to reduce the amount of power needed to power the RF ID tag memory device 157. Accordingly, the reduced power requirement allows the use of small batteries and small portable battery powered metering devices, making it more comfortable for the user to carry the integrated system in his pocket.

When using RF ID tag 157 to code meter 130 with lot specific information, such information can be transferred directly into the meter's memory (not shown) so that the RF tag 157 is read only once on insertion or attachment, thus auto-coding the meter for use. This method is non-technique dependent or evident to the user, eliminating common coding errors associated with forgetting to change the code chip or button code on older technologies. Strips cannot be mixed among different containers due to container strip lot code association. In addition, the RF tag 157 can be programmed quickly after manufacturing information is known. The RF tag 157 can also be disabled when a preset number of tests are completed. One having ordinary skill in the art will understand that many other stored parameters may disable RF tag 157, i.e. strip specific test parameters, manufacture, test type, etc.

Although the on-container coding methods described above are designed to prevent meter calibration errors, the integrated diagnostic test system 100 further employs additional safeguards to minimize the chance that a user will mistakenly use meter 130 with test media from a brand or lot for which the meter 130 has not been calibrated. For example, the integrated diagnostic system 100 can include one or more preventive measures that may disable one or more functions of the meter upon the occurrence of certain triggering events. For instance, the preventive measure may render meter 130 wholly inoperative after the meter 130 has been used for a certain period of time or quantity of tests, or with a certain quantity of test media. The meter 130 may then be simply disposed of or returned to the manufacturer for remanufacturing. Alternatively, the preventive measure may render only the diagnostic testing function of a controller (not shown) inoperative, or simply prevent the meter from displaying the result of a diagnostic test. The user may then retain meter 130 in order to use its remaining functions. One having ordinary skill in the art will understand that many other safeguards may be employed to minimize and prevent meter calibration errors.

3. Refillable Test Strip Container

Figure 27:
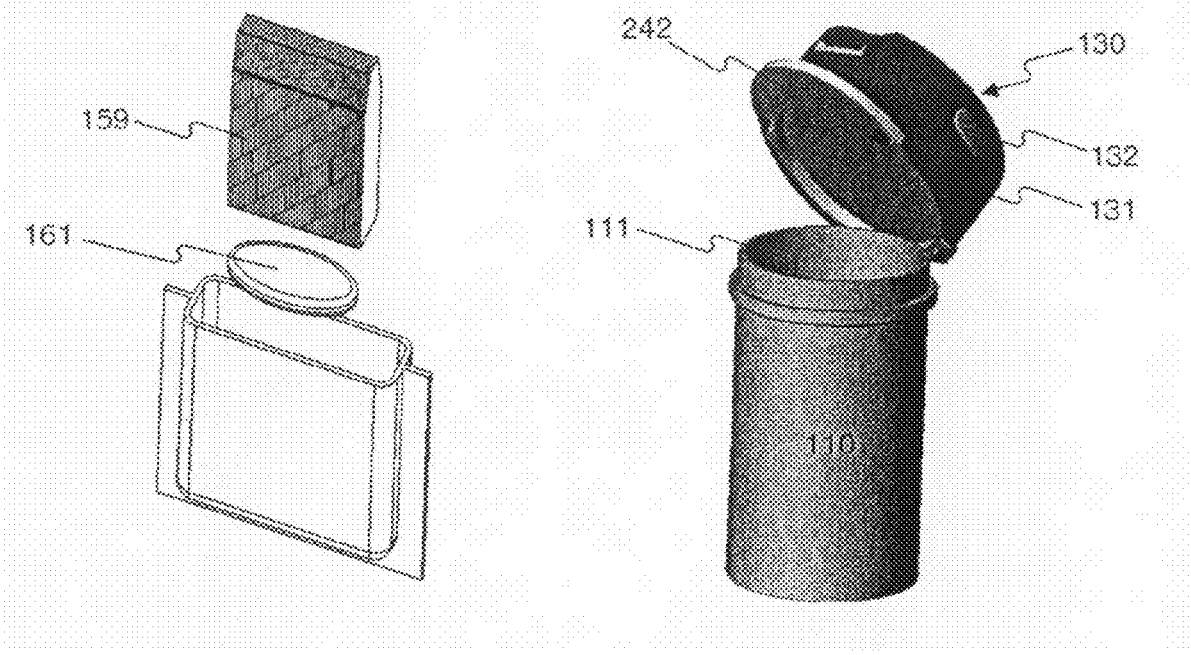
FIG. 27 is a perspective view of a foil pouch with a desiccant pill used to refill a refillable test strip container.

As illustrated in FIG. 27, exemplary integrated diagnostic test system 100 includes a container 110 for containing test media, such as test strips 120, and a meter 130 for performing a diagnostic test using the test strips 120 contained in container 110. Integrated system 100 may further include a foil pouch of test strips 159 with a desiccant pill 161 that can be used to refill test strip container 110, thus saving the cost of replacing container 110 with attached meter 130. The user can simply purchase a foil pouch of test strips 159 with a desiccant pill 161 to refill container 110 when empty. This refill method can be used with any on-container coding method described above, including use with coded contact pads 147, coded memory chips 151, and RF ID tag devices 157.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A container for a diagnostic testing system, consisting essentially of:
    a magazine arranged in the container, the magazine having a first surface and a second surface configured at opposite ends thereof, the magazine being configured to house a plurality of test media;
    a first positioning device arranged on or near the first surface of the magazine and configured to push the plurality of test media toward the second surface of the magazine; and
    a self-contained meter for performing a diagnostic test on a sample applied to one of the plurality of test media, the meter having a closure portion shaped to conform to and press-fit with an opening of the container, and configured to selectively unseal and reseal the opening of the container.

2. The container of claim 1, wherein the first positioning device includes a spring.

3. The container of claim 1, wherein the magazine includes a dispensing mechanism arranged on or near the second surface of the magazine and configured to dispense one or more, of the plurality of test media.

4. The container of claim 3, wherein the dispensing mechanism is a manually-operated sliding mechanism configured to slide the one or more of the plurality of test media toward an aperture in a third surface of the magazine.

5. The container of claim 3, wherein the dispensing mechanism is an electromechanically-operated sliding mechanism configured to slide the one or more of the plurality of test media toward an aperture in a third surface of the magazine.

6. The container of claim 3, wherein the dispensing mechanism is an electromechanically-operated rotating mechanism configured to displace the one or more of the plurality of test media toward an aperture in a third surface of the magazine.

7. The container of claim 1, wherein the magazine has a substantially rectangular internal cross-section.

8. A container for a diagnostic testing system, consisting essentially of:
   a magazine removably arranged in the container, the magazine having a first surface and a second surface configured at opposite ends thereof, the magazine being configured to house a plurality of test media;
   a first positioning device arranged on or near the first surface of the magazine and configured to push the plurality of test media toward the second surface of the magazine;
   a second positioning device arranged between a bottom exterior surface of the magazine and a bottom interior surface of the container; and
   a self-contained meter for performing a diagnostic test on a sample applied to one of the plurality of test media, the meter having a closure portion shaped to conform to and press-fit with an opening of the container, and configured to selectively unseal and reseal the opening of the container.

9. The container of claim 8, wherein the magazine includes a media retaining device arranged on a top portion of the magazine.

10. The container of claim 9, wherein the media retaining device includes at least two edges configured to retain the plurality of test media while allowing a user to enter in contact with at least a top one of the plurality of test media.

11. The container of claim 8, wherein the first positioning device includes a spring.

12. The container of claim 8, wherein the second positioning device includes a spring.

13. The container of claim 11, wherein the second positioning device includes a spring.

14. The container of claim 8, wherein the second positioning device is configured to let the magazine protrude from the container to allow a user to obtain at least one of the plurality of test media, when the closure portion of the meter is in an open position, and to compress sufficiently to allow the magazine to fit within the container, when the closure portion of the meter is in a closed position.

15. The container of claim 8, wherein the magazine has a substantially rectangular internal cross-section.

16. The container of claim 8, wherein the magazine is configured to house at least 50 test media.

17. The container of claim 8, wherein the magazine includes a coding element.

18. The container of claim 8, wherein each of the plurality of test media includes a coding element.

19. The container of claim 1, further comprising a detector arranged on or near the second surface of the magazine for detecting a position of the one or more of the plurality of test media displaced toward an aperture of the magazine.

20. The container of claim 8, further comprising a detector arranged on or near the second surface of the magazine for detecting a position of the one or more of the plurality of test media displaced toward an aperture of the magazine.

* * * * *